(12) United States Patent
Ginn

(10) Patent No.: US 7,842,068 B2
(45) Date of Patent: Nov. 30, 2010

(54) APPARATUS AND METHODS FOR PROVIDING TACTILE FEEDBACK WHILE DELIVERING A CLOSURE DEVICE

(75) Inventor: Richard S. Ginn, San Jose, CA (US)

(73) Assignee: Integrated Vascular Systems, Inc., Redwood City, CA (US)

( * ) Notice: Subject to any disclaimer, the term of this patent is extended or adjusted under 35 U.S.C. 154(b) by 989 days.

(21) Appl. No.: 10/006,400

(22) Filed: Nov. 30, 2001

(65) Prior Publication Data

US 2002/0072768 A1 Jun. 13, 2002

Related U.S. Application Data

(63) Continuation-in-part of application No. 09/732,835, filed on Dec. 7, 2000, now Pat. No. 6,780,197.

(51) Int. Cl.
*A61B 17/08* (2006.01)
*A61D 1/00* (2006.01)

(52) U.S. Cl. ..................................... 606/213
(58) Field of Classification Search .............. 606/1, 606/215–221, 213, 139–159, 190–200; 128/887; 600/201–210
See application file for complete search history.

(56) References Cited

U.S. PATENT DOCUMENTS

| 287,046 | A | 10/1883 | Norton |
|---|---|---|---|
| 438,400 | A | 10/1890 | Brennen |
| 1,088,393 | A | 2/1914 | Backus |
| 1,331,401 | A | 2/1920 | Summers |
| 1,426,111 | A | 8/1922 | Sacker |
| 1,516,990 | A | 11/1924 | Silverman |
| 1,596,004 | A | 8/1926 | De Bengoa |
| 1,647,958 | A | 11/1927 | Ciarlante |

(Continued)

FOREIGN PATENT DOCUMENTS

CA 2 339 060 2/2000

(Continued)

OTHER PUBLICATIONS

PCT Publication No. WO 99/62408 entitled, "Vascular Port Device", Dec. 9, 1999.

(Continued)

*Primary Examiner*—(Jackie) Tan-Uyen T. Ho
*Assistant Examiner*—Dianne Dornbusch
(74) *Attorney, Agent, or Firm*—Workman Nydegger

(57) ABSTRACT

An apparatus for sealing a passage through tissue includes a tubular member, a plug, and a locator member. The plug is disposed on a distal end of the tubular member and includes an external thread. The locator member is inserted into a lumen of the tubular member until a distal portion is disposed beyond the plug. The distal portion includes a helically wound wire and a tether coupled to the wire that is movable for causing the wire to buckle. To seal a passage communicating with a blood vessel, the distal portion of the locator member is inserted into the passage, and the plug is threaded into the passage until the distal portion extends into the vessel. The tether is pulled to buckle the wire, and the plug is unthreaded until the buckled wire contacts a wall of the vessel, whereupon the plug is released to seal the passage.

54 Claims, 11 Drawing Sheets

U.S. PATENT DOCUMENTS

| | | |
|---|---|---|
| 1,847,347 A | 3/1932 | Maisto |
| 1,852,098 A | 4/1932 | Anderson |
| 1,880,569 A | 10/1932 | Weis |
| 2,075,508 A | 3/1937 | Davidson |
| 2,087,074 A | 7/1937 | Tucker |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | LeRoy |
| 3,618,447 A | 11/1971 | Goins |
| 3,664,345 A | 5/1972 | Dabbs et al. |
| 3,677,243 A | 7/1972 | Nerz |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,976,079 A | 8/1976 | Samuels et al. |
| 3,985,138 A | 10/1976 | Jarvik |
| 4,014,492 A | 3/1977 | Rothfuss |
| 4,018,228 A | 4/1977 | Goosen |
| 4,064,881 A | 12/1977 | Meredith |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |

| | | | | | | |
|---|---|---|---|---|---|---|
| 5,108,421 A | 4/1992 | Fowler | | 5,392,978 A | 2/1995 | Velez et al. |
| 5,114,032 A | 5/1992 | Laidlaw | | 5,395,030 A | 3/1995 | Kuramoto et al. |
| 5,114,065 A | 5/1992 | Storace | | 5,409,499 A | 4/1995 | Yi |
| 5,116,349 A | 5/1992 | Aranyi | | 5,411,520 A | 5/1995 | Nash et al. |
| 5,122,122 A | 6/1992 | Allgood | | 5,413,571 A | 5/1995 | Katsaros et al. |
| 5,122,156 A | 6/1992 | Granger et al. | | 5,413,584 A | 5/1995 | Schulze |
| 5,131,379 A | 7/1992 | Sewell, Jr. | | 5,416,584 A | 5/1995 | Kay |
| 5,147,381 A | 9/1992 | Heimerl et al. | | 5,417,699 A | 5/1995 | Klein et al. |
| 5,156,609 A | 10/1992 | Nakao et al. | | 5,419,777 A | 5/1995 | Hofling |
| 5,158,566 A | 10/1992 | Pianetti | | 5,423,857 A | 6/1995 | Rosenman et al. |
| 5,160,339 A | 11/1992 | Chen et al. | | 5,425,489 A | 6/1995 | Shichman et al. |
| 5,167,634 A | 12/1992 | Corrigan, Jr. et al. | | 5,425,740 A | 6/1995 | Hutchinson, Jr. |
| 5,167,643 A | 12/1992 | Lynn | | 5,431,639 A | 7/1995 | Shaw |
| 5,171,249 A | 12/1992 | Stefanchik et al. | | 5,431,667 A | 7/1995 | Thompson et al. |
| 5,171,250 A | 12/1992 | Yoon | | 5,433,721 A | 7/1995 | Hooven et al. |
| 5,171,251 A | 12/1992 | Bregen et al. | | 5,437,631 A * | 8/1995 | Janzen ............... 604/506 |
| 5,176,648 A | 1/1993 | Holmes et al. | | 5,439,479 A | 8/1995 | Shichman et al. |
| 5,176,682 A | 1/1993 | Chow | | 5,443,477 A | 8/1995 | Marin et al. |
| 5,192,288 A | 3/1993 | Thompson et al. | | 5,443,481 A | 8/1995 | Lee |
| 5,192,300 A | 3/1993 | Fowler | | 5,449,359 A | 9/1995 | Groiso |
| 5,192,301 A | 3/1993 | Kamiya et al. | | 5,456,400 A | 10/1995 | Shichman et al. |
| 5,192,302 A | 3/1993 | Kensey et al. | | 5,462,558 A | 10/1995 | Kolesa et al. |
| 5,192,602 A | 3/1993 | Spencer et al. | | 5,462,561 A | 10/1995 | Voda |
| 5,203,787 A | 4/1993 | Noblitt et al. | | 5,466,241 A | 11/1995 | Leroy et al. |
| 5,209,756 A | 5/1993 | Seedhorm et al. | | 5,470,010 A | 11/1995 | Rothfuss et al. |
| 5,217,024 A | 6/1993 | Dorsey et al. | | 5,474,557 A | 12/1995 | Mai |
| 5,219,359 A | 6/1993 | McQuilkin et al. | | 5,474,572 A | 12/1995 | Hayhurst |
| 5,222,974 A | 6/1993 | Kensey et al. | | 5,478,352 A | 12/1995 | Fowler |
| 5,226,908 A | 7/1993 | Yoon | | 5,478,353 A | 12/1995 | Yoon et al. |
| 5,234,449 A | 8/1993 | Bruker et al. | | 5,478,354 A | 12/1995 | Tovey et al. |
| 5,236,435 A | 8/1993 | Sewell, Jr. | | 5,486,195 A | 1/1996 | Myers et al. |
| 5,236,445 A | 8/1993 | Hayhurst et al. | | 5,497,933 A | 3/1996 | DeFonzo et al. |
| 5,242,457 A | 9/1993 | Akopov et al. | | 5,501,698 A | 3/1996 | Roth et al. |
| 5,242,459 A | 9/1993 | Buelna | | 5,507,744 A | 4/1996 | Tay et al. |
| 5,243,857 A | 9/1993 | Janota | | 5,507,755 A | 4/1996 | Gresl et al. |
| 5,246,156 A | 9/1993 | Rothfuss et al. | | 5,514,159 A | 5/1996 | Matula et al. |
| 5,246,443 A | 9/1993 | Mai | | 5,521,184 A | 5/1996 | Zimmermann |
| 5,250,058 A | 10/1993 | Miller et al. | | 5,522,840 A | 6/1996 | Krajicek |
| 5,254,105 A | 10/1993 | Haaga | | 5,527,322 A | 6/1996 | Klein et al. |
| 5,258,015 A | 11/1993 | Li et al. | | 5,536,251 A | 7/1996 | Evard et al. |
| 5,269,792 A | 12/1993 | Kovac et al. | | 5,540,712 A | 7/1996 | Kleshinski et al. |
| 5,275,616 A | 1/1994 | Fowler | | 5,540,716 A | 7/1996 | Hlavacek |
| 5,282,808 A | 2/1994 | Kovac et al. | | 5,543,520 A | 8/1996 | Zimmermann |
| 5,282,827 A | 2/1994 | Kensey et al. | | 5,544,802 A | 8/1996 | Crainich |
| 5,282,832 A | 2/1994 | Toso et al. | | 5,547,474 A | 8/1996 | Kloeckl et al. |
| 5,289,963 A | 3/1994 | McGarry et al. | | 5,560,532 A | 10/1996 | DeFonzo et al. |
| 5,290,243 A | 3/1994 | Chodorow et al. | | 5,571,120 A | 11/1996 | Yoon |
| 5,290,310 A | 3/1994 | Makower et al. | | 5,575,771 A | 11/1996 | Walinsky |
| 5,292,309 A | 3/1994 | Van Tassel et al. | | 5,584,879 A | 12/1996 | Reimold et al. |
| 5,292,332 A | 3/1994 | Lee | | 5,591,205 A | 1/1997 | Fowler |
| 5,304,184 A | 4/1994 | Hathaway et al. | | 5,593,412 A | 1/1997 | Martinez et al. |
| 5,304,204 A | 4/1994 | Bregen | | 5,593,422 A | 1/1997 | Muijs Van de Moer et al. |
| 5,306,254 A | 4/1994 | Nash et al. | | 5,593,425 A | 1/1997 | Bonutti et al. |
| 5,306,280 A | 4/1994 | Bregen et al. | | 5,601,602 A | 2/1997 | Fowler |
| 5,318,542 A | 6/1994 | Hirsch et al. | | 5,609,597 A | 3/1997 | Lehrer |
| 5,320,639 A | 6/1994 | Rudnick | | 5,611,986 A | 3/1997 | Datta et al. |
| 5,330,442 A | 7/1994 | Green et al. | | 5,613,974 A | 3/1997 | Andreas et al. |
| 5,330,445 A | 7/1994 | Haaga | | 5,618,291 A | 4/1997 | Thompson et al. |
| 5,334,216 A | 8/1994 | Vidal et al. | | 5,618,306 A | 4/1997 | Roth et al. |
| 5,334,217 A | 8/1994 | Das | | 5,620,452 A | 4/1997 | Yoon |
| 5,335,680 A | 8/1994 | Moore | | 5,620,461 A | 4/1997 | Muijs et al. |
| 5,340,360 A | 8/1994 | Stefanchik | | 5,630,824 A | 5/1997 | Hart |
| 5,350,399 A | 9/1994 | Erlebacher et al. | | 5,643,318 A | 7/1997 | Tsukernik et al. |
| 5,352,229 A | 10/1994 | Goble et al. | | 5,645,553 A | 7/1997 | Kolesa et al. |
| 5,364,406 A | 11/1994 | Sewell, Jr. | | 5,645,565 A | 7/1997 | Rudd et al. |
| 5,364,408 A | 11/1994 | Gordon | | 5,645,566 A | 7/1997 | Brenneman et al. |
| 5,366,458 A | 11/1994 | Korthoff et al. | | 5,645,567 A | 7/1997 | Crainich |
| 5,366,479 A | 11/1994 | McGarry et al. | | 5,649,959 A | 7/1997 | Hannam et al. |
| 5,376,101 A | 12/1994 | Green et al. | | D383,539 S | 9/1997 | Croley |
| 5,383,896 A | 1/1995 | Gershony et al. | | 5,669,917 A | 9/1997 | Sauer et al. |
| 5,383,905 A | 1/1995 | Golds et al. | | 5,674,231 A * | 10/1997 | Green et al. ............ 606/142 |
| RE34,866 E | 2/1995 | Kensey et al. | | 5,676,689 A | 10/1997 | Kensey et al. |
| 5,391,173 A | 2/1995 | Wilk | | 5,676,974 A | 10/1997 | Valdes et al. |

| | | |
|---|---|---|
| 5,681,334 A | 10/1997 | Evans et al. |
| 5,681,351 A | 10/1997 | Jamiolkowski et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,700,273 A | 12/1997 | Buelna et al. |
| 5,709,708 A | 1/1998 | Thal |
| 5,716,375 A | 2/1998 | Fowler |
| 5,720,755 A | 2/1998 | Dakov |
| 5,720,765 A | 2/1998 | Thal |
| 5,725,498 A | 3/1998 | Janzen et al. |
| 5,725,552 A | 3/1998 | Kotula et al. |
| 5,725,554 A | 3/1998 | Simon et al. |
| 5,725,556 A | 3/1998 | Moser et al. |
| 5,728,109 A | 3/1998 | Schulze et al. |
| 5,728,110 A | 3/1998 | Vidal et al. |
| 5,728,114 A | 3/1998 | Evans et al. |
| 5,728,122 A | 3/1998 | Leschinsky et al. |
| 5,728,132 A | 3/1998 | Van Tassel et al. |
| 5,732,872 A | 3/1998 | Bolduc et al. |
| 5,735,873 A | 4/1998 | MacLean |
| 5,735,875 A | 4/1998 | Bonutti et al. |
| 5,735,877 A | 4/1998 | Pagedas |
| 5,749,898 A | 5/1998 | Schulze et al. |
| 5,752,966 A | 5/1998 | Chang |
| 5,755,726 A | 5/1998 | Pratt et al. |
| 5,755,778 A | 5/1998 | Kleshinski |
| 5,766,217 A | 6/1998 | Christy |
| 5,766,246 A | 6/1998 | Mulhauser et al. |
| 5,769,862 A | 6/1998 | Kammerer et al. |
| 5,769,870 A | 6/1998 | Salahieh et al. |
| 5,776,150 A | 7/1998 | Nolan et al. |
| 5,779,707 A | 7/1998 | Bertholet et al. |
| 5,782,844 A | 7/1998 | Yoon et al. |
| 5,782,860 A | 7/1998 | Epstein et al. |
| 5,782,861 A | 7/1998 | Cragg et al. |
| 5,782,864 A | 7/1998 | Lizardi |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,810,776 A | 9/1998 | Bacich et al. |
| 5,810,846 A | 9/1998 | Virnich et al. |
| 5,810,851 A | 9/1998 | Yoon |
| 5,810,877 A | 9/1998 | Roth et al. |
| 5,814,069 A | 9/1998 | Schulze et al. |
| 5,817,113 A | 10/1998 | Gifford |
| 5,820,631 A | 10/1998 | Nobles |
| 5,827,298 A | 10/1998 | Hart et al. |
| 5,830,125 A | 11/1998 | Scribner et al. |
| 5,833,698 A | 11/1998 | Hinchliffe et al. |
| 5,843,167 A | 12/1998 | Dwyer et al. |
| 5,846,254 A | 12/1998 | Schulze et al. |
| 5,853,421 A * | 12/1998 | Leschinsky et al. ......... 606/213 |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,005 A | 1/1999 | Kontos |
| 5,868,755 A | 2/1999 | Kanner et al. |
| 5,868,763 A | 2/1999 | Spence et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,525 A | 2/1999 | Edwards et al. |
| 5,873,876 A | 2/1999 | Christy |
| 5,879,366 A | 3/1999 | Shaw et al. |
| 5,893,592 A | 4/1999 | Schulze et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,919,208 A | 7/1999 | Valenti |
| 5,922,009 A | 7/1999 | Epstein et al. |
| 5,935,147 A * | 8/1999 | Kensey et al. ............... 606/213 |
| 5,938,667 A | 8/1999 | Peyser et al. |
| 5,941,890 A | 8/1999 | Voegele et al. |
| 5,947,999 A | 9/1999 | Groiso |
| 5,951,518 A | 9/1999 | Licata et al. |
| 5,951,576 A | 9/1999 | Wakabayashi |
| 5,951,589 A | 9/1999 | Epstein et al. |
| 5,957,936 A | 9/1999 | Yoon et al. |
| 5,957,938 A | 9/1999 | Zhu et al. |
| 5,964,782 A | 10/1999 | LaFontaine et al. |
| 5,976,159 A | 11/1999 | Bolduc et al. |
| 5,976,161 A | 11/1999 | Kirsch et al. |
| 5,984,934 A | 11/1999 | Ashby et al. |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,013,084 A | 1/2000 | Ken et al. |
| 6,022,372 A | 2/2000 | Kontos |
| 6,024,750 A | 2/2000 | Mastri |
| 6,024,758 A | 2/2000 | Thal |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,063,085 A | 5/2000 | Tay et al. |
| 6,063,114 A | 5/2000 | Nash et al. |
| 6,066,160 A | 5/2000 | Colvin et al. |
| 6,071,300 A | 6/2000 | Brenneman et al. |
| 6,074,409 A | 6/2000 | Goldfarb |
| 6,077,281 A | 6/2000 | Das |
| 6,077,291 A | 6/2000 | Das |
| 6,080,182 A | 6/2000 | Shaw |
| 6,080,183 A | 6/2000 | Tsugita et al. |
| 6,086,608 A | 7/2000 | Ek et al. |
| 6,090,130 A | 7/2000 | Nash et al. |
| 6,092,561 A | 7/2000 | Schmid |
| 6,099,553 A | 8/2000 | Hart et al. |
| 6,102,271 A | 8/2000 | Longo et al. |
| 6,106,545 A | 8/2000 | Egan |
| 6,110,184 A | 8/2000 | Weadock |
| 6,113,612 A | 9/2000 | Swanson et al. |
| 6,117,125 A | 9/2000 | Rothbarth et al. |
| 6,117,148 A | 9/2000 | Ravo |
| 6,120,524 A | 9/2000 | Taheri |
| 6,126,675 A | 10/2000 | Shchervinsky et al. |
| 6,126,677 A | 10/2000 | Ganaja et al. |
| 6,136,010 A | 10/2000 | Modesitt et al. |
| 6,143,017 A | 11/2000 | Thal |
| 6,149,660 A | 11/2000 | Laufer et al. |
| 6,149,667 A | 11/2000 | Hovland et al. |
| 6,152,144 A | 11/2000 | Lesh et al. |
| 6,152,934 A | 11/2000 | Harper et al. |
| 6,152,936 A | 11/2000 | Christy et al. |
| 6,152,937 A | 11/2000 | Peterson et al. |
| 6,159,234 A | 12/2000 | Bonutti et al. |
| 6,165,204 A | 12/2000 | Levinson et al. |

| Patent No. | Date | Inventor |
|---|---|---|
| 6,174,324 B1 | 1/2001 | Egan et al. |
| 6,193,734 B1 | 2/2001 | Bolduc et al. |
| 6,197,042 B1 * | 3/2001 | Ginn et al. ............ 606/213 |
| 6,200,329 B1 | 3/2001 | Fung et al. |
| 6,203,565 B1 | 3/2001 | Bonutti et al. |
| 6,206,913 B1 | 3/2001 | Yencho et al. |
| 6,220,248 B1 | 4/2001 | Voegele et al. |
| 6,221,102 B1 | 4/2001 | Baker et al. |
| 6,231,592 B1 | 5/2001 | Bonutti et al. |
| 6,248,124 B1 | 6/2001 | Pedros et al. |
| 6,254,615 B1 | 7/2001 | Bolduc et al. |
| 6,254,617 B1 | 7/2001 | Spence et al. |
| 6,254,642 B1 | 7/2001 | Taylor |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,305,891 B1 | 10/2001 | Burlingame |
| 6,319,258 B1 | 11/2001 | McAllen, III et al. |
| 6,322,580 B1 | 11/2001 | Kanner |
| 6,334,865 B1 | 1/2002 | Redmond et al. |
| 6,348,064 B1 | 2/2002 | Kanner |
| 6,358,258 B1 | 3/2002 | Arcia et al. |
| D457,958 S | 5/2002 | Dycus |
| 6,383,208 B1 | 5/2002 | Sancoff et al. |
| 6,391,048 B1 * | 5/2002 | Ginn et al. ............ 606/213 |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,423,054 B1 | 7/2002 | Ouchi |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,517,569 B2 | 2/2003 | Mikus et al. |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,569,173 B1 | 5/2003 | Blatter et al. |
| 6,569,185 B2 | 5/2003 | Ungs |
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,599,303 B1 | 7/2003 | Peterson et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,616,686 B2 | 9/2003 | Coleman et al. |
| 6,623,509 B2 | 9/2003 | Ginn |
| 6,623,510 B2 | 9/2003 | Carley et al. |
| 6,626,918 B1 * | 9/2003 | Ginn et al. ............ 606/148 |
| 6,632,238 B2 | 10/2003 | Ginn et al. |
| 6,634,537 B2 | 10/2003 | Chen |
| 6,645,205 B2 | 11/2003 | Ginn |
| 6,652,538 B2 | 11/2003 | Kayan et al. |
| 6,652,556 B1 | 11/2003 | VanTassel et al. |
| 6,663,655 B2 | 12/2003 | Ginn et al. |
| 6,669,714 B2 | 12/2003 | Coleman et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,749,621 B2 | 6/2004 | Pantages et al. |
| 6,749,622 B2 | 6/2004 | McGuckin et al. |
| 6,755,842 B2 | 6/2004 | Kanner et al. |
| 6,767,356 B2 | 7/2004 | Kanner et al. |
| 6,780,197 B2 | 8/2004 | Roe et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,926,723 B1 | 8/2005 | Mulhauser et al. |
| 6,926,731 B2 | 8/2005 | Coleman et al. |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,083,635 B2 | 8/2006 | Ginn |
| 7,108,709 B2 | 9/2006 | Cummins |
| 7,108,710 B2 | 9/2006 | Anderson |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,533,790 B1 | 5/2009 | Knodel et al. |
| 7,597,706 B2 | 10/2009 | Kanner et al. |
| D611,144 S | 3/2010 | Reynolds |
| 2001/0007077 A1 | 7/2001 | Ginn et al. |
| 2001/0031972 A1 | 10/2001 | Robertson et al. |
| 2001/0046518 A1 | 11/2001 | Sawhney |
| 2001/0047180 A1 | 11/2001 | Grudem et al. |
| 2002/0026208 A1 | 2/2002 | Roe et al. |
| 2002/0026215 A1 | 2/2002 | Redmond et al. |
| 2002/0038127 A1 | 3/2002 | Blatter et al. |
| 2002/0042622 A1 | 4/2002 | Vargas et al. |
| 2002/0049472 A1 | 4/2002 | Coleman et al. |
| 2002/0058960 A1 | 5/2002 | Hudson et al. |
| 2002/0072768 A1 * | 6/2002 | Ginn .................. 606/213 |
| 2002/0077657 A1 | 6/2002 | Ginn et al. |
| 2002/0082641 A1 | 6/2002 | Ginn et al. |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |

| Publication No. | Date | Inventor |
|---|---|---|
| 2002/0151921 A1 | 10/2002 | Kanner et al. |
| 2002/0193808 A1 | 12/2002 | Belef et al. |
| 2003/0004543 A1 | 1/2003 | Gleeson et al. |
| 2003/0009180 A1 | 1/2003 | Hinchliffe et al. |
| 2003/0009196 A1 | 1/2003 | Peterson |
| 2003/0032981 A1 | 2/2003 | Kanner et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0158577 A1 | 8/2003 | Ginn et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2004/0009205 A1 | 1/2004 | Sawhney |
| 2004/0009289 A1 | 1/2004 | Carley et al. |
| 2004/0010285 A1 | 1/2004 | Carley et al. |
| 2004/0039414 A1 | 2/2004 | Carley et al. |
| 2004/0073236 A1 | 4/2004 | Carley et al. |
| 2004/0073255 A1 | 4/2004 | Ginn et al. |
| 2004/0082906 A1 | 4/2004 | Tallarida et al. |
| 2004/0087985 A1 | 5/2004 | Loshakove et al. |
| 2004/0092964 A1 | 5/2004 | Modesitt et al. |
| 2004/0092968 A1 | 5/2004 | Caro et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0059982 A1 | 3/2005 | Zung et al. |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1* | 4/2005 | Ravlkumar ................ 606/213 |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0165357 A1 | 7/2005 | McGuckin et al. |
| 2005/0177189 A1 | 8/2005 | Ginn et al. |
| 2005/0216057 A1 | 9/2005 | Coleman et al. |
| 2005/0222614 A1 | 10/2005 | Ginn et al. |
| 2005/0234508 A1 | 10/2005 | Cummins et al. |
| 2005/0245876 A1 | 11/2005 | Khosravi et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0034930 A1 | 2/2006 | Khosravi et al. |
| 2006/0047313 A1 | 3/2006 | Khanna et al. |
| 2006/0100664 A1 | 5/2006 | Pai et al. |
| 2006/0135989 A1 | 6/2006 | Carley et al. |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0253037 A1 | 11/2006 | Ginn et al. |
| 2006/0253072 A1 | 11/2006 | Pai et al. |
| 2006/0265012 A1 | 11/2006 | Anderson |
| 2006/0287674 A1 | 12/2006 | Ginn et al. |
| 2007/0010853 A1 | 1/2007 | Ginn et al. |
| 2007/0010854 A1 | 1/2007 | Cummins |
| 2007/0021778 A1 | 1/2007 | Carly |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0123817 A1 | 5/2007 | Khosravi et al. |
| 2007/0203506 A1 | 8/2007 | Sibbitt, Jr. et al. |
| 2007/0250080 A1 | 10/2007 | Jones et al. |
| 2008/0004636 A1 | 1/2008 | Walberg |
| 2008/0009794 A1 | 1/2008 | Bagaoisan et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0221616 A1 | 9/2008 | Ginn et al. |
| 2008/0312686 A1 | 12/2008 | Ellingwood |
| 2008/0319475 A1 | 12/2008 | Clark |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0254119 A1 | 10/2009 | Sibbitt, Jr. et al. |
| 2010/0130965 A1 | 5/2010 | Sibbitt, Jr. |

FOREIGN PATENT DOCUMENTS

| | | | |
|---|---|---|---|
| DE | 197 11 288 | 1/1998 | |
| DE | 297 23 736 U 1 | 4/1999 | |
| DE | 19859952 | 2/2000 | |
| EP | 0 386 361 | 9/1990 | |
| EP | 0 534 696 | 3/1993 | |
| EP | 0 756 851 | 2/1997 | |
| EP | 0 774 237 A2 * | 5/1997 | ................ 606/142 |
| EP | 0 858 776 | 8/1998 | |
| EP | 0 941 697 | 9/1999 | |
| FR | 2 443 238 | 7/1980 | |
| FR | 2 715 290 | 7/1995 | |
| FR | 2 722 975 | 2/1996 | |
| FR | 2 768 324 | 3/1999 | |
| GB | 1 358 466 | 7/1974 | |
| GB | 2 075 144 | 11/1981 | |
| IE | S 2000/0722 | 10/2001 | |
| IE | S 2000/0724 | 10/2001 | |
| IE | S 2001/0547 | 7/2002 | |
| IE | S 2001/0815 | 7/2002 | |
| IE | S 2001/0748 | 8/2002 | |
| IE | S 2001/0749 | 8/2002 | |
| IE | S 2002/0452 | 12/2002 | |
| IE | S 2002/0664 | 2/2003 | |
| IE | S 2002/0665 | 2/2003 | |
| IE | S 2002/0451 | 7/2003 | |
| IE | S 2002/0552 | 7/2003 | |
| IE | S 2003/0424 | 12/2003 | |
| IE | S 2003/0490 | 1/2004 | |
| IE | S 2004/0368 | 11/2005 | |
| IE | S 2005/0342 | 11/2005 | |
| JP | 58-181006 | 12/1983 | |
| JP | 12 74750 | 11/1989 | |
| JP | 11500642 | 8/1997 | |
| JP | 2000102546 | 4/2000 | |
| NL | 9302140 | 7/1995 | |
| PL | 171425 | 4/1997 | |
| RU | 2086192 | 8/1997 | |
| SU | 197801 | 6/1967 | |
| SU | 495067 | 12/1975 | |
| SU | 912155 | 3/1982 | |

| | | |
|---|---|---|
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 A1 | 8/1996 |
| WO | WO 97/07741 | 3/1997 |
| WO | WO 95/21573 | 8/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/25508 | 6/1998 |
| WO | WO 98/58591 | 12/1998 |
| WO | WO 99/21491 | 5/1999 |
| WO | WO 99/60941 | 12/1999 |
| WO | WO 99/62415 | 12/1999 |
| WO | WO 00/06029 | 2/2000 |
| WO | WO 00/07505 | 2/2000 |
| WO | WO 00/27311 | 5/2000 |
| WO | WO 00/27313 | 5/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/98302 | 12/2002 |
| WO | WO 03/071957 | 1/2003 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/094748 | 11/2003 |
| WO | WO 03/101310 | 12/2003 |
| WO | WO 2004/004578 | 1/2004 |
| WO | WO 2004/060169 | 7/2004 |
| WO | WO 2004/069054 | 8/2004 |
| WO | WO 2005/000126 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2008/031102 A1 | 3/2008 |
| WO | WO 2009/079091 | 6/2009 |
| WO | WO 2010/031050 | 3/2010 |
| ZA | 20010527 | 1/2001 |
| ZA | 200100528 | 1/2001 |

OTHER PUBLICATIONS

PCT Publication No. WO 00/060029 entitled, "Expansile Device for Use in Blood Vessels and Tracts in the Body and Method", Feb. 10, 2000.
PCT Publication No. WO 00/07640 entitled, "Vascular Suction Cannula, Dilator and Surgical Stapler", Feb. 17, 2000.
PCT Publication No. WO 00/07640, "Vascular Suction Cannula, Dialator and Surgical Stapler", Feb. 17, 2000.
PCT Publication No. WO 00/56227, entitled "Advanced Closure Device", Sep. 28, 2000.
PCT Publication No. WO 00/56223 entitled "Vascular Closure Device", Sep. 28, 2000.
PCT Publication No. WO 99/62408 entitled "Vascular Port Device", Dec. 9, 1999.
PCT Publication No. WO 98/24374, "Vascular Wound Closure System", Yong Zhu, et al., Jun. 11, 1998.
PCT Publication No. WO 97/20505, "Vascular Wound Closure Device", Yong Zhu, et al., Jun. 12, 1997.
"Hand tool for forming telephone connections—comprises pliers with reciprocably driven ram crimping clip around conductors against anvil", Derwent-ACC-No. 1978-B8090A.
Database WPI; Section PQ, Week 200120; Derwent Publications Ltd., London GB; AN 2001-203165; XP002199926 & ZA 200 100 528 A (Anthony T), Feb. 28, 2001 abstract.
U.S. Appl. No. 09/866,551, filed May 25, 2001.
U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
Stretch Comb by Scunci, retrieved via internet at www.scunci.com/productdetail by examiner on Oct. 9, 2007, publication date unavailable.
U.S. Appl. No. 12/106,928, filed Apr. 21, 2008, Ginn et al.
U.S. Appl. No. 12/106,937, filed Apr. 21, 2008, Ginn et al.
U.S. Appl. No. 12/113,092, filed Apr. 30, 2008, Ginn et al.
U.S. Appl. No. 12/113,851, filed May 1, 2008, Coleman et al.
U.S. Appl. No. 12/114,031, filed May 2, 2008, Coleman et al.
U.S. Appl. No. 12/114,091, filed May 2, 2008, Coleman et al.
U.S. Appl. No. 12/143,020, filed Jun. 20, 2008, Ellingwood et al.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
Deepak Mital et al, Renal Transplantation Without Sutures Using The Vascular Clipping System For Renal Artery And Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 7—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H DE Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.

J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.

Jeremy L Gilbert PhD, Wound Closure Biomaterials And Devices, Shock., Mar. 1999, p. 226, vol. 11—No. 3, Institution Northwestern University.

Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.

K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.

MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.

Michael Gianturco, A Play on Catheterization, Forbes, Dec. 1996, p. 146, vol. 158—No. 15.

OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.

P M N Werker, et al, Review of facilitated approaches to vascular anastomosis surgery, Conference: Utrecht MICABG Workshop 2, The Annals of thoracic surgery, Apr. 1996, pp. S122-127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

SA Beyer-Enke et al, Immediate sealing of arterial puncture site following femoropopliteal angioplasty: A prospective randomized trial, Cardiovascular And Interventional Radiology 1996, Nov.-Dec. 1996, pp. 406-410, vol. 19—No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, Vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-28, Vol. 5—No. 3-4.

UT Aker et al, Immediate arterial hemostasis after cardiac catheterization: initial experience with a new puncture closure device, Cathet Cardiovasc Diagn, Mar. 1994, pp. 228-232, Vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 10/147,774, mailed Feb. 4, 2008, Notice of Allowance.
U.S. Appl. No. 10/147,774, mailed Jun. 30, 2008, Office Action.
U.S. Appl. No. 10/264,306, mailed May 26, 2005, Office Action.
U.S. Appl. No. 10/264,306, mailed Feb. 4, 2008, Notice of Allowance.
U.S. Appl. No. 10/264,306, mailed Jun. 27, 2008, Office Action.
U.S. Appl. No. 10/356,214, mailed Mar. 6, 2008, Office Action.
U.S. Appl. No. 10/435,104, mailed Apr. 4, 2008, Notice of Allowance.
U.S. Appl. No. 10/435,104, mailed Sep. 26, 2008, Notice of Allowance.
U.S. Appl. No. 10/517,004, mailed Jan. 30, 2008, Office Action.
U.S. Appl. No. 10/541,083, mailed May 5, 2008, Office Action.
U.S. Appl. No. 10/541,083, mailed Sep. 19, 2008, Notice of Allowance.
U.S. Appl. No. 10/616,832, mailed Sep. 17, 2008, Office Action.
U.S. Appl. No. 10/638,115, mailed Feb. 7, 2008, Office Action.
U.S. Appl. No. 10/667,144, mailed May 12, 2008, Office Action.
U.S. Appl. No. 10/682,459, mailed Apr. 2, 2008, Office Action.
U.S. Appl. No. 10/786,444, mailed Apr. 24, 2008, Office Action.
U.S. Appl. No. 10/787,073, mailed Feb. 22, 2008, Office Action.
U.S. Appl. No. 11/113,549, mailed Apr. 16, 2008, Office Action.
U.S. Appl. No. 11/152,562, mailed May 13, 2008, Office Action.
U.S. Appl. No. 11/198,811, mailed Aug. 26, 2008, Office Action.
U.S. Appl. No. 11/344,891, mailed Apr. 29, 2008, Office Action.
U.S. Appl. No. 11/406,203, mailed May 23, 2008, Notice of Allowance.
U.S. Appl. No. 11/406,203, mailed Sep. 22, 2008, Notice of Allowance.
U.S. Appl. No. 11/411,925, mailed Feb. 5, 2008, Office Action.
U.S. Appl. No. 11/532,325, mailed Feb. 23, 2009, Office Action.
U.S. Appl. No. 11/744,089, mailed Nov. 26, 2008, Office Action.
U.S. Appl. No. 12/106,928, mailed Jan. 23, 2009, Office Action.
U.S. Appl. No. 12/106,937, mailed Mar. 30, 2009, Office Action.
U.S. Appl. No. 29/296,370, mailed Aug. 18, 2008, Office Action.
U.S. Appl. No. 29/296,370, mailed Dec. 2, 2008, Notice Of Allowance.
U.S. Appl. No 29/296,370, mailed Apr. 1, 2009, Notice Of Allowance.
U.S. Appl. No. 60/696,069, filed Jul. 1, 2005, Pantages et al.
U.S. Appl. No. 60/694,026, filed Jun. 25, 2007, Ellingwood.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
McCarthy, et al., "Tension (Stay) Suture Bridge", J. of International College of Surgeons, 34(5), pp. 613-614 (Nov. 1960). cited by other.
U.S. Appl. No. 09/680,837, mailed Jul. 9, 2002, Office Action.
U.S. Appl. No. 09/680,837, mailed Nov. 6, 2002, Office Action.
U.S. Appl. No. 09/680,837, mailed Mar. 25, 2003, Office Action.

U.S. Appl. No. 09/680,837, mailed Jun. 16, 2003, Notice of Allowance.
U.S. Appl. No. 09/680,837, mailed Sep. 11, 2003, Issue Notification.
U.S. Appl. No. 10/147,774, mailed Mar. 18, 2009, Office Action.
U.S. Appl. No. 10/264,306, mailed Feb. 26, 2009, Office Action.
U.S. Appl. No. 10/305,923, mailed Nov. 1, 2004, Office Action.
U.S. Appl. No. 10/305,923, mailed Mar. 3, 2005, Notice of Allowance.
U.S. Appl. No. 10/356,214 mailed Nov. 4, 2008, Office Action.
U.S. Appl. No. 10/356,214, mailed Apr. 29, 2009, Office Action.
U.S. Appl. No. 10/435,104, mailed Nov. 14, 2007, Notice of Allowance.
U.S. Appl. No. 10/435,104, mailed Dec. 22, 2008, Notice Of Allowance.
U.S. Appl. No. 10/517,004, mailed Aug. 13, 2008, Notice Of Allowance.
U.S. Appl. No. 10/517,004, mailed Feb. 10, 2009, Notice Of Allowance.
U.S. Appl. No. 10/541,083, mailed Oct. 31, 2007, Office Action.
U.S. Appl. No. 10/541,083, mailed Dec. 29, 2008, Notice Of Allowance.
U.S. Appl. No. 10/638,115, mailed Oct. 29, 2008, Office Action.
U.S. Appl. No. 10/667,144, mailed Mar. 24, 2009, Office Action.
U.S. Appl. No. 10/669,313, mailed Oct. 31, 2005, Office Action.
U.S. Appl. No. 10/669,313, mailed Jan. 11, 2006, Notice Of Allowance.
U.S. Appl. No. 10/669,313, mailed Jun. 28, 2006, Notice Of Allowance.
U.S. Appl. No. 10/669,313, mailed Nov. 15, 2006, Issue Notification.
U.S. Appl. No. 10/682,459, mailed Dec. 4, 2008, Office Action.
U.S. Appl. No. 10/786,444, mailed Oct. 17, 2008, Office Action.
U.S. Appl. No. 10/787,073, mailed Nov. 12, 2008, Office Action.
U.S. Appl. No. 10/908,721, mailed Nov. 25, 2008, Office Action.
U.S. Appl. No. 11/048,503, mailed Mar. 13, 2009, Office Action.
U.S. Appl. No. 11/152,562, mailed Feb. 13, 2009, Office Action.
U.S. Appl. No. 11/344,793, mailed Jan. 22, 2009, Office Action.
U.S. Appl. No. 11/344,868, mailed Mar. 25, 2009, Office Action.
U.S. Appl. No. 11/344,891, mailed Dec. 8, 2008, Office Action.
U.S. Appl. No. 11/344,891, mailed Feb. 26, 2009, Office Action.
U.S. Appl. No. 11/396,731, mailed Feb. 13, 2009, Office Action.
U.S. Appl. No. 11/406,203, mailed Mar. 3, 2009, Office Action.
U.S. Appl. No. 11/411,925, mailed Jan. 12, 2009, Office Action.
U.S. Appl. No. 11/427,297, mailed Jan. 30, 2009, Office Action.
U.S. Appl. No. 11/461,323, mailed May 2, 2007, Office Action.
U.S. Appl. No. 11/461,323, mailed Oct. 29, 2007, Office Action.
U.S. Appl. No. 11/461,323, mailed Apr. 25, 2008, Office Action.
U.S. Appl. No. 11/461,323, mailed Nov. 6, 2008, Office Action.
U.S. Appl. No. 10/264,306, mailed Aug. 13, 2009, Office Action.
U.S. Appl. No. 10/517,004, mailed Jun. 26, 2009, Notice of Allowance.
U.S. Appl. No. 10/541,083, mailed Apr. 16, 2009, Notice of Allowance.
U.S. Appl. No. 10/616,832, mailed Jul. 21, 2009, Office Action.
U.S. Appl. No. 10/638,115, mailed May 7, 2009, Notice of Allowance.
U.S. Appl. No. 10/682,459, mailed Jun. 10, 2009, Office Action.
U.S. Appl. No. 10/786,444, mailed Jun. 18, 2009, Office Action.
U.S. Appl. No. 10/787,073, mailed Aug. 13, 2009, Office Action.
U.S. Appl. No. 10/908,721, mailed Jun. 23, 2009, Office Action.
U.S. Appl. No. 11/048,503, Jun. 26, 2009, Office Action.
U.S. Appl. No. 11/113,549, mailed Jul. 21, 2009, Office Action.
U.S. Appl. No. 11/152,562, mailed Jul. 6, 2009, Office Action.
U.S. Appl. No. 11/198,811, mailed Sep. 22, 2009, Office Action.
U.S. Appl. No. 11/390,586, mailed Jun. 24, 2009, Office Action.
U.S. Appl. No. 11/396,141, mailed May 22, 2009, Restriction Requirement.
U.S. Appl. No. 11/396,141, mailed Aug. 26, 2009, Office Action.
U.S. Appl. No. 11/396,731, mailed May 22, 2009, Office Action.
U.S. Appl. No. 11/406,203, mailed Sep. 16, 2009, Office Action.
U.S. Appl. No. 11/411,925, mailed Sep. 10, 2009, Office Action.
U.S. Appl. No. 11/427,297, mailed Sep. 15, 2009, Office Action.
U.S. Appl. No. 11/461,323, mailed Jul. 27, 2009, Office Action.
U.S. Appl. No. 11/532,325, mailed Jun. 17, 2009, Office Action.
U.S. Appl. No. 11/744,089, mailed Aug. 14, 2009, Office Action.
U.S. Appl. No. 11/958,295, mailed Aug. 27, 2009, Office Action.
U.S. Appl. No. 60/693,531, filed Jun. 24, 2005, Carly.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
Taber's Cyclopedic Medical Dictionary, 18th Ed. 1997, pp. 747 and 1420.
U.S. Appl. No. 10/147,774, mailed Oct. 26, 2009, Office Action.
U.S. Appl. No. 10/264,306, Jan. 27, 2010, Office Action.
U.S. Appl. No. 10/356,214, mailed Jan. 13, 2010, Notice of Allowance.
U.S. Appl. No. 10/435,104, mailed Jan. 20, 2010, Notice of Allowance.
U.S. Appl. No. 10/517,004, mailed Jan. 11, 2010, Notice of Allowance.
U.S. Appl. No. 10/541,083, mailed Feb. 5, 2010, Notice of Allowance.
U.S. Appl. No. 10/616,832, mailed Jan. 11, 2010, Notice of Allowance.
U.S. Appl. No. 10/541,083, mailed Sep. 30, 2009, Notice of Allowance.
U.S. Appl. No. 10/638,115, mailed Dec. 1, 2009, Notice of Allowance.
U.S. Appl. No. 10/638,115, mailed Apr. 2, 2010, Notice of Allowance.
U.S. Appl. No. 10/667,144, mailed Nov. 23, 2009, Office Action.
U.S. Appl. No. 10/682,459, mailed Dec. 23, 2009, Office Action.
U.S. Appl. No. 10/786,444, mailed Jan. 14, 2010, Office Action.
U.S. Appl. No. 10/787,073, mailed Feb. 17, 2010, Notice of Allowance.
U.S. Appl. No. 10/908,721, mailed Feb. 2, 2010, Office Action.
U.S. Appl. No. 11/048,503, mailed Jan. 11, 2010, Notice of Allowance.
U.S. Appl. No. 11/344,891, mailed Oct. 7, 2009, Office Action.
U.S. Appl. No. 11/455,993, mailed Feb. 17, 2009, Office Action.
U.S. Appl. No. 11/455,993, mailed Dec. 16, 2009, Office Action.
U.S. Appl. No. 11/461,323, mailed Apr. 5, 2010, Notice of Allowance.
U.S. Appl. No. 11/532,325, mailed Jan. 5, 2010, Office Action.
U.S. Appl. No. 11/532,576, mailed Mar. 1, 2010, Restriction Requirement.
U.S. Appl. No. 11/675,462, mailed Dec. 10, 2009, Office Action.
U.S. Appl. No. 11/767,818, mailed Dec. 24, 2009, Restriction Requirement.
U.S. Appl. No. 11/767,818, mailed Mar. 22, 2010, Office Action.
U.S. Appl. No. 11/959,334, mailed Aug. 19, 2009, Office Action.
U.S. Appl. No. 11/959,334, mailed Jan. 12, 2010, Notice of Allowance.
U.S. Appl. No. 12/106,937, mailed Nov. 18, 2009, Office Action.
U.S. Appl. No. 12/106,928, mailed Oct. 5, 2009, Office Action.
U.S. Appl. No. 12/402,398, mailed Mar. 9, 2010, Restriction Requirement.
U.S. Appl. No. 12/403,256, mailed Dec. 16, 2009, Restriction Requirement.
U.S. Appl. No. 29/296,370, mailed Feb. 10, 2010, Issue Notification.
U.S. Appl. No. 60/711,279, filed Aug. 24, 2005, Sibbitt, Jr. et al.
U.S. Appl. No. 60/726,985, filed Oct. 14, 2005, Sibbitt, Jr. et al.
U.S. Appl. No. 60/793,444, filed Apr. 20, 2006, Jones et al.
U.S. Appl. No. 61/097,072, filed Sep. 15, 2008, Sibbitt, Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.
U.S. Appl. No. 10/147,774, mailed Jun. 8, 2010, Office Action.
U.S. Appl. No. 10/264,306, mailed Jun. 15, 2010, Office Action.
U.S. Appl. No. 10/356,214, mailed May 13, 2010, Notice of Allowance.
U.S. Appl. No. 10/435,104, mailed Jun. 2, 2010, Office Action.
U.S. Appl. No. 10/517,004, mailed Apr. 23, 2010, Notice of Allowance.
U.S. Appl. No. 10/541,083, mailed May 10, 2010, Notice of Allowance.

U.S. Appl. No. 10/616,832, mailed May 12, 2010, Notice of Allowance.
U.S. Appl. No. 10/667,144, mailed Jun. 22, 2010, Office Action.
U.S. Appl. No. 10/682,459, mailed Apr. 28, 2010, Office Action.
U.S. Appl. No. 11/048,503, mailed Apr. 26, 2010, Notice of Allowance.
U.S. Appl. No. 11/113,549, mailed Jul. 6, 2010, Office Action.
U.S. Appl. No. 11/152,562, mailed Mar. 31, 2010, Office Action.
U.S. Appl. No. 11/198,811, mailed Jun. 29, 2010, Notice of Allowance.
U.S. Appl. No. 11/316,775, mailed Apr. 16, 2008, Office Action.
U.S. Appl. No. 11/316,775, mailed Aug. 6, 2008, Office Action.
U.S. Appl. No. 11/344,891, mailed May 7, 2010, Office Action.
U.S. Appl. No. 11/390,586, mailed Jul. 6, 2010, Office Action.
U.S. Appl. No. 11/396,141, mailed May 4, 2010, Office Action.
U.S. Appl. No. 11/396,731, mailed Jun. 29, 2010, Office Action.
U.S. Appl. No. 11/406,203, mailed Jun. 18, 2010, Notice of Allowance.
U.S. Appl. No. 11/508,656, mailed Dec. 9, 2009, Office Action.
U.S. Appl. No. 11/508,656, mailed Mar. 25, 2010, Office Action.
U.S. Appl. No. 11/508,662, mailed Dec. 28, 2009, Office Action.
U.S. Appl. No. 11/508,662, mailed Apr. 14, 2010, Office Action.
U.S. Appl. No. 11/508,715, mailed Jan. 6, 2010, Office Action.
U.S. Appl. No. 11/508,715, mailed Apr. 26, 2010, Office Action.
U.S. Appl. No. 11/532,576, mailed Apr. 23, 2010, Office Action.
U.S. Appl. No. 11/674,930, mailed Jan. 8, 2009, Office Action.
U.S. Appl. No. 11/674,930, mailed Jun. 4, 2009, Office Action.
U.S. Appl. No. 11/674,930, mailed Jan. 8, 2010, Office Action.
U.S. Appl. No. 11/852,190, mailed Jun. 24, 2010, Office Action.
U.S. Appl. No. 11/958,295, mailed May 25, 2010, Office Action.
U.S. Appl. No. 11/959,334, mailed Apr. 14, 2010, Notice of Allowance.
U.S. Appl. No. 12/106,928, mailed May 10, 2010, Office Action.
U.S. Appl. No. 12/113,851, mailed Apr. 27, 2010, Office Action.
U.S. Appl. No. 12/113,851, mailed Jun. 24, 2010, Office Action.
U.S. Appl. No. 12/402,398, mailed May 20, 2010, Office Action.
U.S. Appl. No. 12/403,256, mailed Mar. 30, 2010, Office Action.
U.S. Appl. No. 12/403,277, mailed Jul. 8, 2010, Office Action.
U.S. Appl. No. 10/435,104, mailed Jul. 23, 2009, Notice of Allowance.
U.S. Appl. No. 11/959,334, mailed Jul. 23, 2010, Notice of Allowance.

* cited by examiner

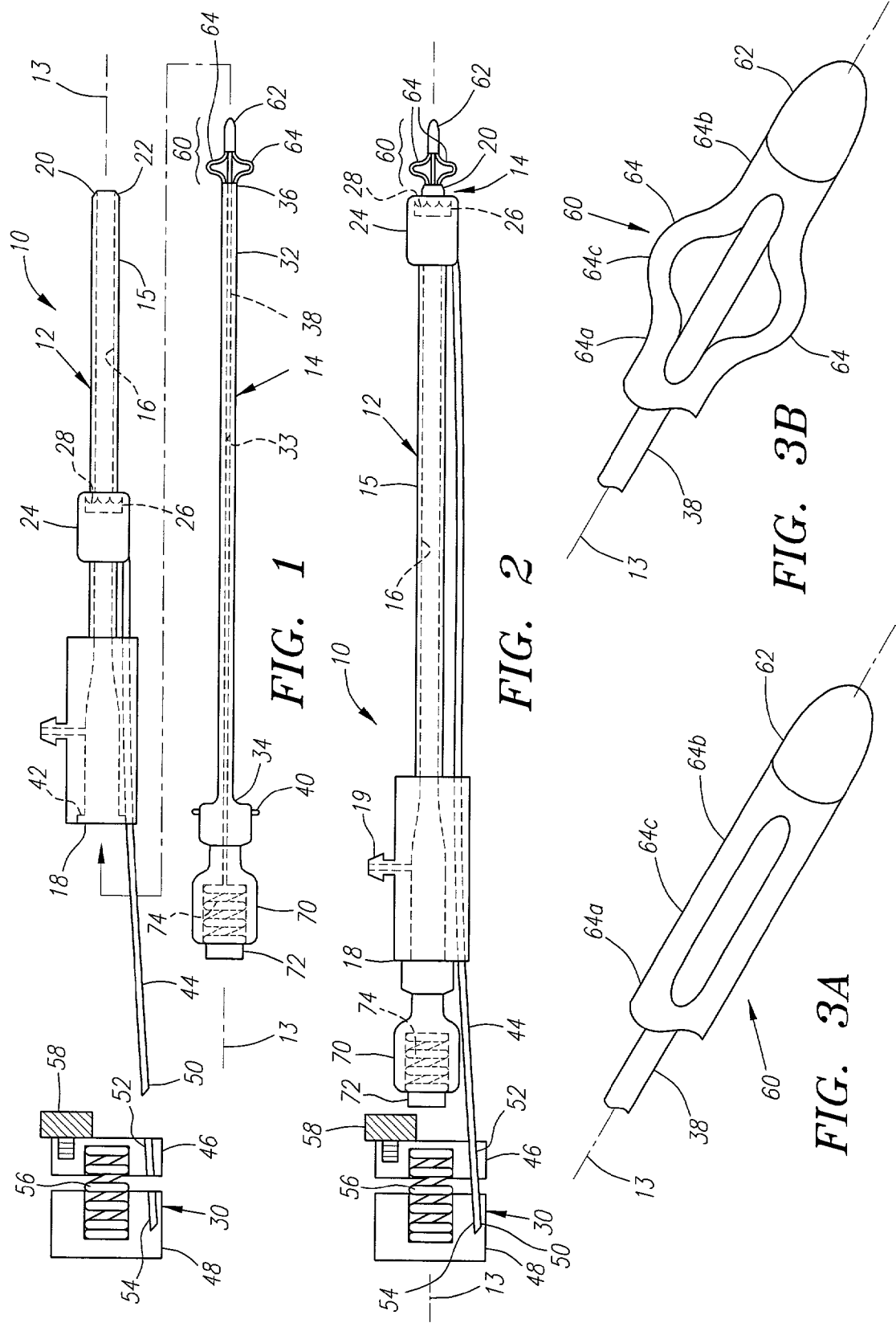

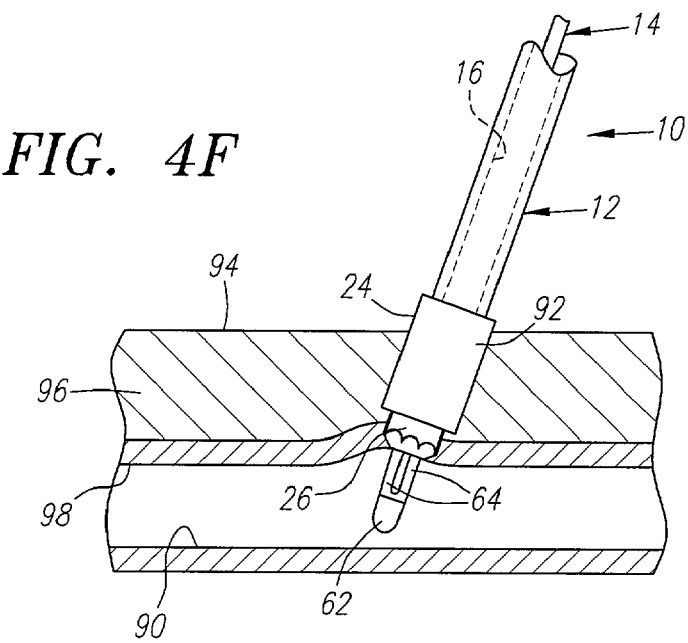
FIG. 4F
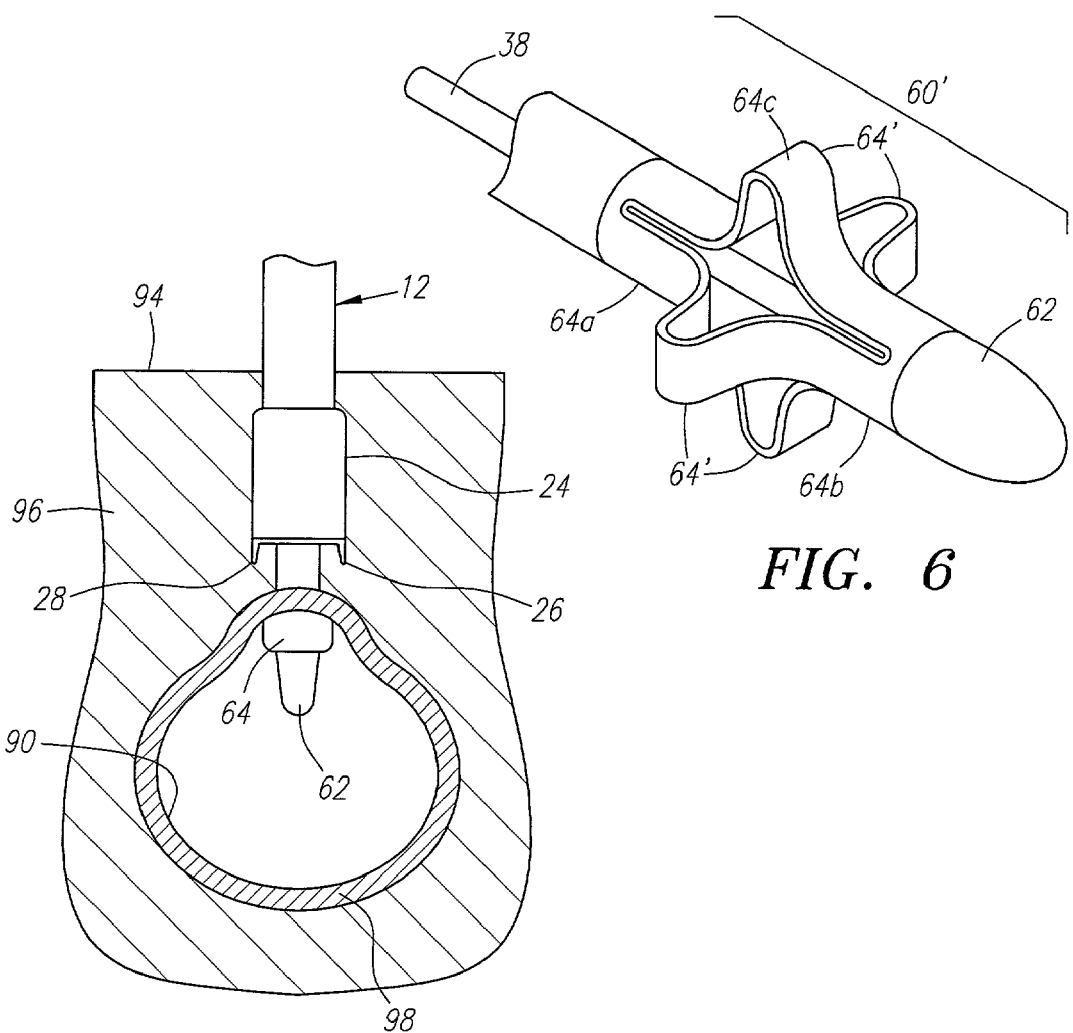
FIG. 6
FIG. 5

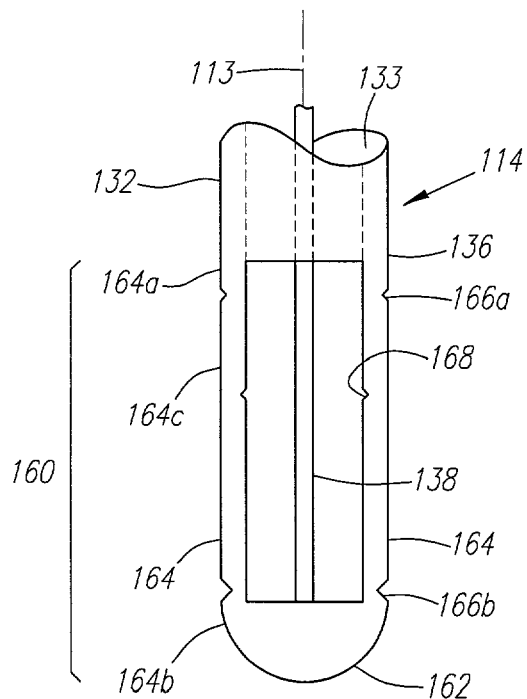
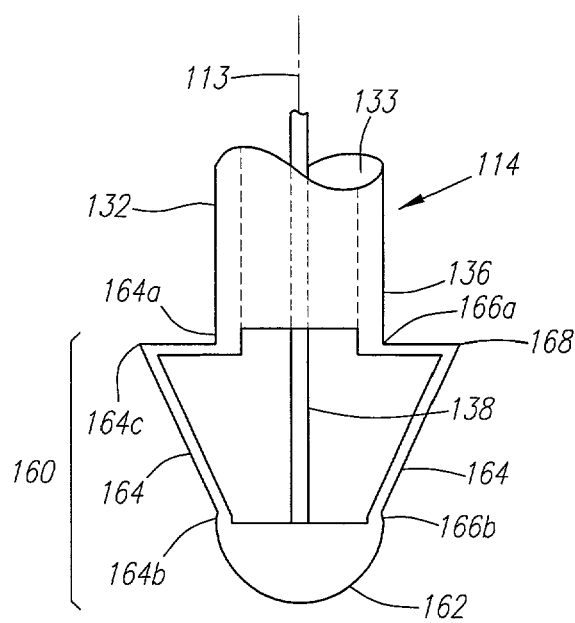
FIG. 7A
FIG. 7B
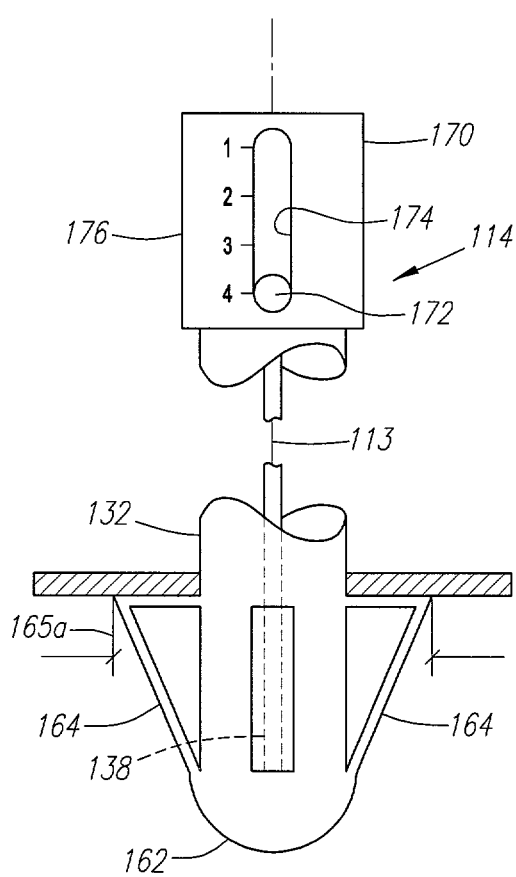
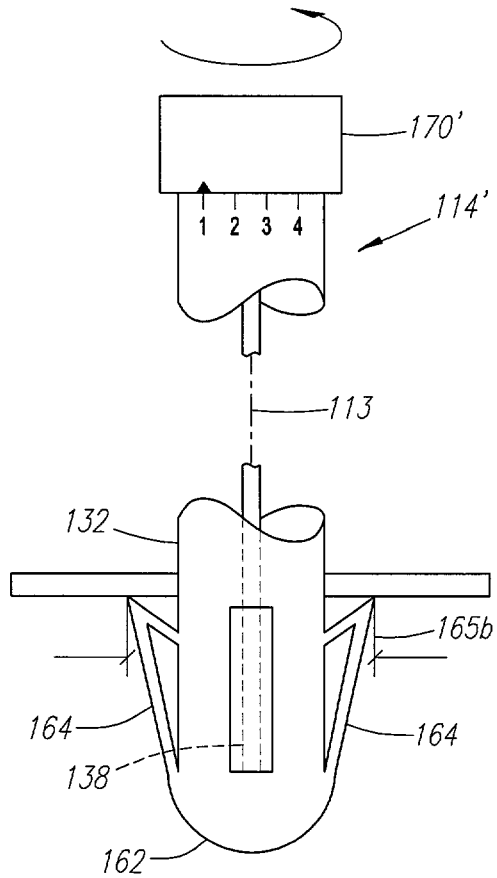
FIG. 8A
FIG. 8B

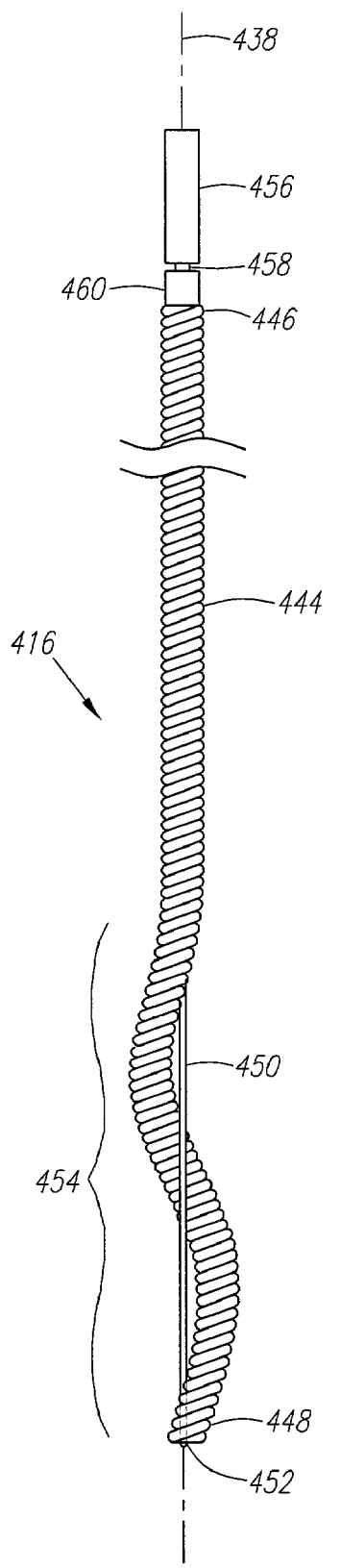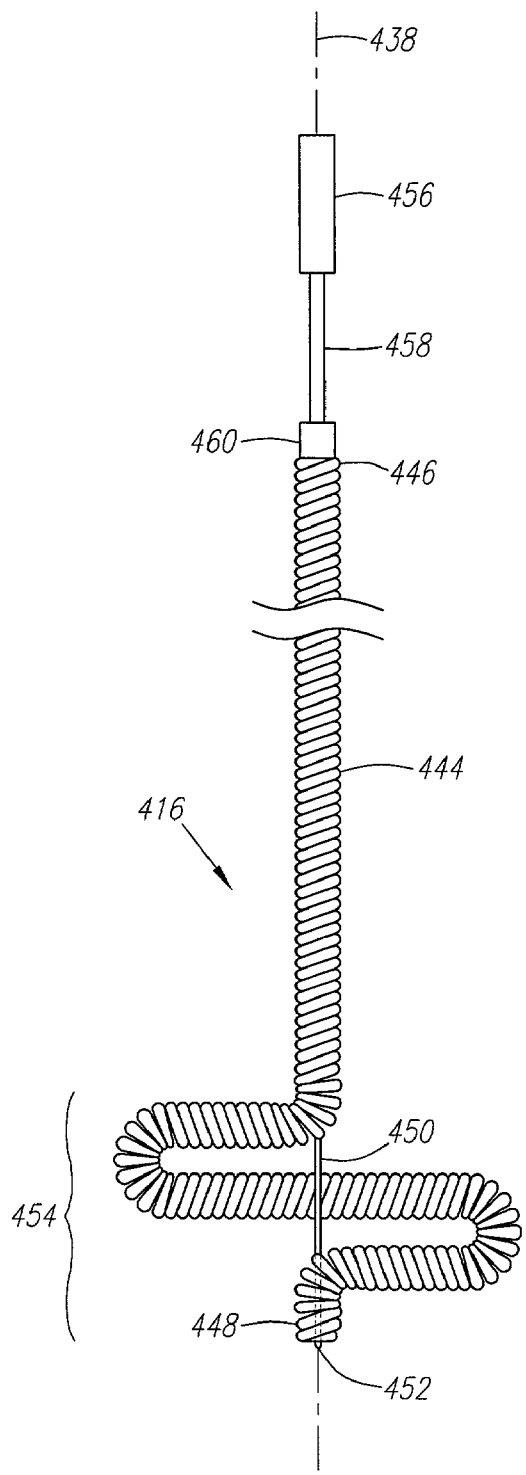
FIG. 11A
FIG. 11B

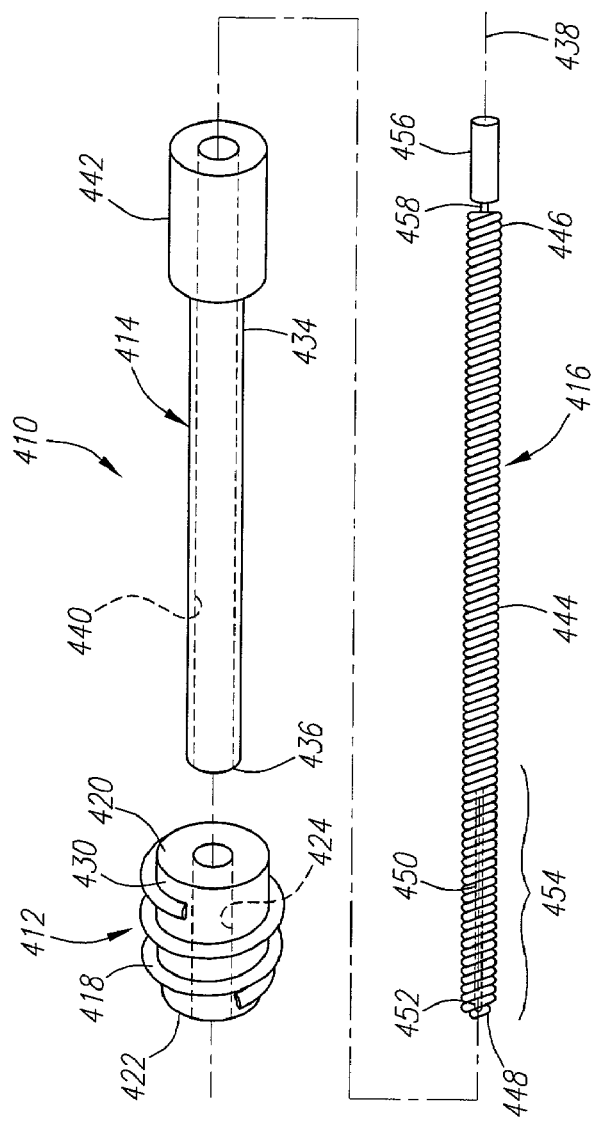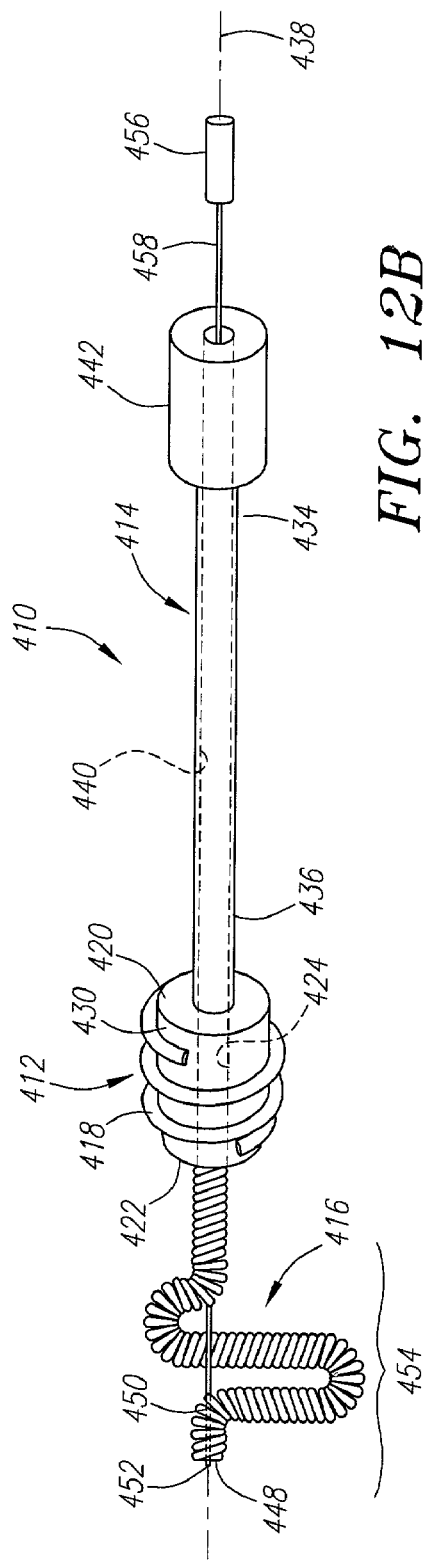

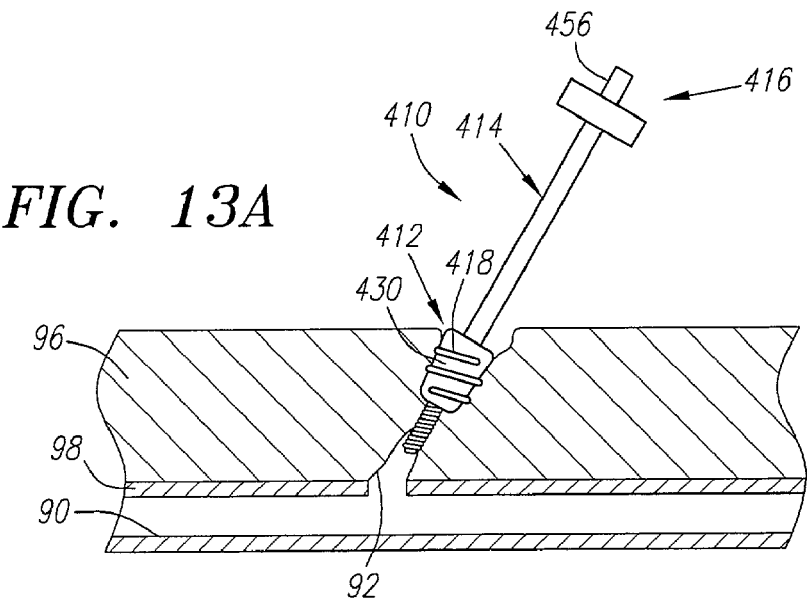
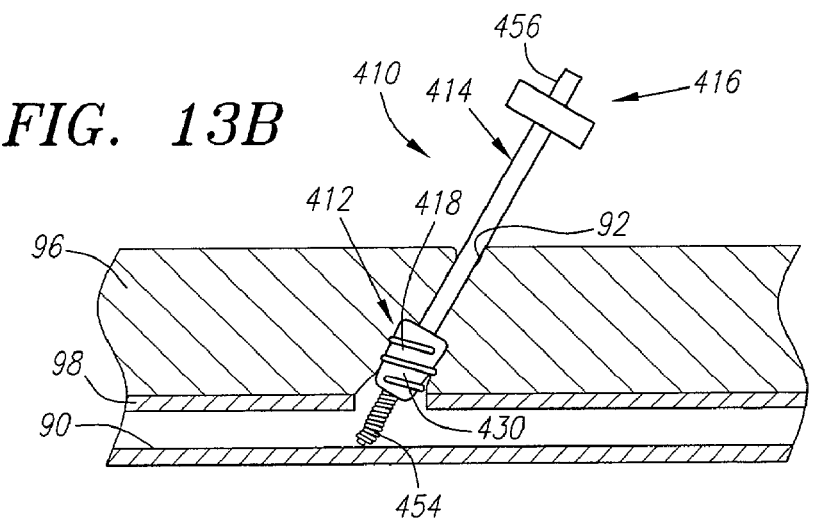
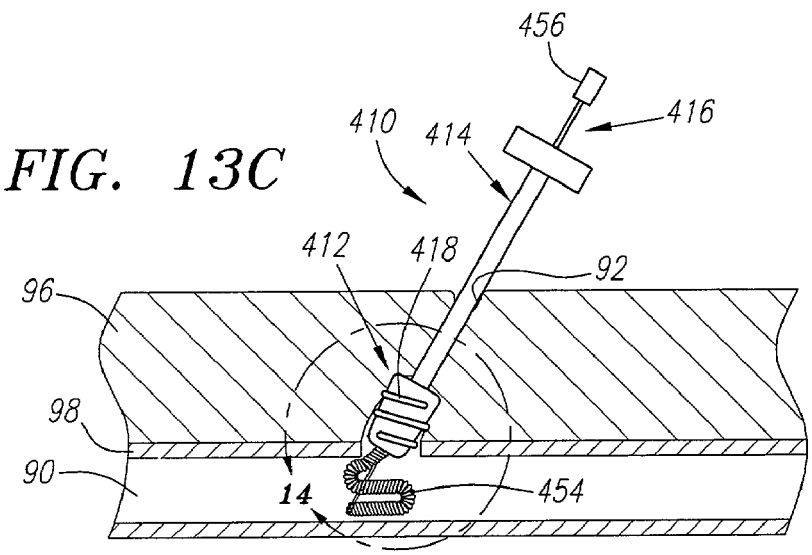

APPARATUS AND METHODS FOR PROVIDING TACTILE FEEDBACK WHILE DELIVERING A CLOSURE DEVICE

This application is a continuation-in-part of application Ser. No. 09/732,835, filed Dec. 7, 2000, now U.S. Pat. No. 6,780,197 the disclosure of which is expressly incorporated herein by reference.

FIELD OF THE INVENTION

The present invention relates generally to apparatus and methods for sealing or closing passages through tissue, particularly to devices for delivering a closure device within a passage communicating with a body lumen, such as a blood vessel, and more particularly to apparatus and methods for positioning such a device relative to the body lumen before delivery.

BACKGROUND

Catheterization and interventional procedures, such as angioplasty or stenting, generally are performed by inserting a hollow needle through a patient's skin and muscle tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

Staples and surgical clips have also been suggested for closing wounds or other openings in tissue. For example, U.S. Pat. Nos. 5,007,921 and 5,026,390, issued to Brown, disclose staples that may be used to close a wound or incision.

In addition, skin seals have been proposed that may be threaded into an opening in skin. For example, U.S. Pat. No. 5,645,565, issued to Rudd et al., discloses a surgical plug that may be screwed into a puncture to seal the puncture. The surgical plug includes an enlarged cap and a threaded shaft that extends from the cap. During an endoscopic procedure, the plug may be threaded into an opening through skin until the cap engages the surface of the skin. The plug is intended to seal the opening communicating with a body cavity to prevent insufflation fluid from leaking from the cavity. Such plugs, however, may only be used at the surface of the skin, and may not be introduced through tissue, for example, to seal an opening in the wall of a blood vessel or other subcutaneous region.

To facilitate positioning devices that are percutaneously inserted into a blood vessel, "bleed back" indicators have been suggested. For example, U.S. Pat. No. 4,317,445, issued to Robinson, discloses a flashback chamber on a first end of a cannula that communicates with a port on a second end. The second end is percutaneously introduced into a patient until the port enters the vessel, whereupon blood, under normal blood pressure, may advance along the cannula and enter the flashback chamber, thereby providing a visual indication that the vessel has been entered. This reference, however, does not discuss vascular wound closure, but is merely directed to an introducer device. In contrast, U.S. Pat. No. 5,676,974, issued to Kensey et al., discloses a bleed back lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel. The loop may also provide a support for facilitating the deployment and deflection of a surgical clip against the vessel wall. Such a device, however, may risk engagement between the loop and the surgical clip, thereby preventing the loop from being withdrawn from the vessel.

Accordingly, apparatus and methods for delivering devices for sealing punctures or other passages through tissue communicating with a blood vessel would be considered useful.

SUMMARY OF THE INVENTION

The present invention is directed to apparatus and methods for delivering devices for sealing or closing passages through tissue, such as punctures communicating with blood vessels or other body lumens, and, more particularly, to apparatus and methods for positioning such devices relative to the body lumens before delivery.

In accordance with one aspect of the present invention, an apparatus is provided for positioning a closure device within a passage through tissue communicating with a body lumen. The apparatus includes an elongate member, e.g., an introducer sheath or other tubular member, including a proximal end, a distal end, and a lumen extending between the proximal and distal ends defining a longitudinal axis.

A closure element is associated with the elongate member for sealing the passage. In a preferred embodiment, the closure element is a plug member disposed on the distal end of the elongate member. The plug member may include a thread pattern on its outer surface, and may include a distal port communicating with a passage therethrough that, in turn, communicates with the lumen in the handle device. A sealing member may be provided in the passage for substantially sealing the passage from fluid flow therethrough. The plug member is preferably releasably attached to the distal end of the elongate member, e.g., by one or more connectors on the distal end of the elongate member and/or on the plug member. Alternatively, the closure element may be a clip that is deployable from the elongate member, e.g., from a housing slidably disposed on the elongate member.

A locator member is provided that may be inserted through the lumen, the locator member having a distal portion that extends distally beyond the distal end of the elongate member when the locator member is fully inserted into the lumen. If the closure element is a plug member, the distal portion also extends beyond the plug member, e.g., through the passage therein.

The locator member includes an elongate deflectable element including a proximal end and a distal end, and a control element coupled to the distal end of the deflectable element. The control element is movable proximally for causing an intermediate portion of the deflectable element, e.g., the distal portion of the locator member, to buckle substantially transversely with respect to the longitudinal axis. In a preferred embodiment, the deflectable element is a helically wound wire and the control member is a tether extending along at least the intermediate portion of the helically wound wire. The tether may extend within the helically wound wire and/or along an outer surface of at least a portion of the helically wound wire. Preferably, the intermediate portion of the deflectable element has a cross-section in its buckled configuration that is larger than a cross-section of the lumen, thereby preventing the deflectable element from being withdrawn into the plug member and/or elongate member once activated.

In accordance with another aspect of the present invention, a method is provided for sealing a passage communicating with a body lumen using an apparatus, such as that described above. The apparatus generally includes an elongate member including proximal and distal ends, and a closure element deployable from the distal end of the elongate member.

A locator member is coupled to the elongate member such that a distal portion of the locator member extends beyond the distal end of the tubular member. For example, if the elongate member is an introducer sheath or other tubular member including a lumen, the locator member may be inserted into the lumen. The distal end of the elongate member is advanced through a patient's skin towards the body lumen via the passage until the distal portion of the locator member is located within the body lumen. For example, if the closure element is a plug member, the elongate member may rotated to thread the plug member into the passage towards the body lumen.

A deflectable element on the distal portion of the locator member is buckled from an axial collapsed configuration to a transverse expanded configuration. The elongate member is manipulated such that the buckled distal portion engages or otherwise contacts a proximal wall of the body lumen, thereby providing a tactile indication of the location of the distal end of the elongate member relative to the body lumen.

The closure device is then deployed from the distal end of the elongate member within the passage. The elongate member and the locator member are then withdrawn from the passage, leaving the closure element to substantially seal the opening.

Preferably, the deflectable element of the locator member includes a helically wound wire, and a tether or other control member coupled to a distal end of the helically wound wire. The tether may be subjected to tension, e.g., directed proximally, to buckle the helically wound wire substantially transversely, thereby defining the transverse configuration.

In a preferred embodiment, the closure element is a plug member releasably coupled to the distal end of the elongate member and including an external thread pattern. If the elongate member is a tubular member, the plug member may include a distal port communicating with the lumen in the tubular member, such that the locator member may be inserted into the tubular member until the distal portion extends through the distal port of the plug member. The distal portion is inserted into the passage until the plug member enters the passage, whereupon the plug member is threaded into the passage until the distal portion of the locator member enters the body lumen. The distal portion may be activated, as described above, and used to provide tactile feedback to position the plug member. For example, the plug member may be at least partially unthreaded before the plug member is deployed within the passage.

In an alternative embodiment, the apparatus may be used in conjunction with an introducer sheath or other tubular member already in place within the passage, e.g., that is used to access the body lumen during a procedure. The locator member may be inserted through the tubular member until the distal portion of the locator member is located within the body lumen. The deflectable element on the distal portion of the locator member may be buckled from an axial collapsed configuration to a transverse expanded configuration. The locator member may be manipulated, e.g., pulled proximally, such that the buckled distal portion engages or otherwise contacts a proximal wall of the body lumen, thereby providing a tactile indication that the distal portion is disposed within the body lumen and/or limiting further proximal movement of the locator member.

A plug member (or other closure device) may then be advanced over the locator member into the passage. For example, the plug member, disposed on the distal end of an elongate member, may be threaded through the tissue along the passage over the locator member. Preferably, the locator member is inserted through the distal port of the plug member and/or through the lumen of the elongate member as the plug member is advanced. Once the plug member attains a desired location within the passage, the plug member may be released from the distal end of the elongate member within the passage. The distal portion of the locator member may be returned to its axial configuration, and the elongate member and the locator member may be withdrawn from the passage, leaving the plug member to substantially seal the opening.

To facilitate positioning of the plug member, the locator member may include one or more markers, e.g., disposed on a proximal portion, that may have a predetermined relation with the distal portion of the locator member. For example, the proximal portion of the locator member may include a marker band located a predetermined distance from the distal portion. The elongate member may include a window for observing the marker when the plug member reaches a predetermined location relative the distal portion, e.g., a predetermined distance proximal to the distal portion. Alternatively, the locator member and the elongate member may include cooperate tactile elements, e.g., tabs and pockets, that engage one another when the plug member reaches a predetermined location. The plug member may then be released at the predetermined location, and then the elongate member and locator member may be removed.

Other objects and features of the present invention will become apparent from consideration of the following description taken in conjunction with the accompanying drawings.

BRIEF DESCRIPTION OF THE DRAWINGS

FIG. 1 is a side view of an apparatus for delivering a closure element, including an introducer sheath, a locator, and an actuator assembly, in accordance with the present invention.

FIG. 2 is a side view of the apparatus of FIG. 1, with the locator disposed within the sheath, and a housing on the sheath advanced to a delivery position.

FIGS. 3A and 3B are perspective views of the distal end of the apparatus of FIGS. 1 and 2, showing positioning elements on the locator in collapsed and expanded configurations, respectively.

FIGS. 4A-4F are cross-sectional views of a blood vessel, showing a method for delivering a closure device into a passage communicating with the vessel.

FIG. 5 is a cross-sectional view of the blood vessel of FIG. 4D, showing the positioning elements engaging a wall of the vessel.

FIG. 6 is a perspective view of an alternate embodiment of a distal portion of the locator with the positioning elements disposed in their expanded configuration.

FIGS. 7A and 7B are side views of another embodiment of a distal portion of a locator with positioning elements disposed in collapsed and expanded configurations, respectively.

FIGS. 8A and 8B are side views of the locator of FIGS. 7A and 7B, including a control on the locator for adjusting the expansion of the positioning elements.

FIGS. 11A and 11B are side views of another preferred embodiment of a locator device, in accordance with the present invention.

FIG. 12A is an exploded perspective view of an apparatus for delivering a closure device, including the locator device of FIGS. 11A and 11B.

FIG. 12B is a perspective view of the apparatus of FIG. 12A after assembly, and with the locator device deployed.

FIGS. 13A-13D are cross-sectional side views, showing a method for delivering a plug member using the apparatus of FIGS. 12A and 12B.

FIG. 13C, showing activation of the locator member with a blood vessel.

DETAILED DESCRIPTION OF THE PREFERRED EMBODIMENTS

Figure 4A:
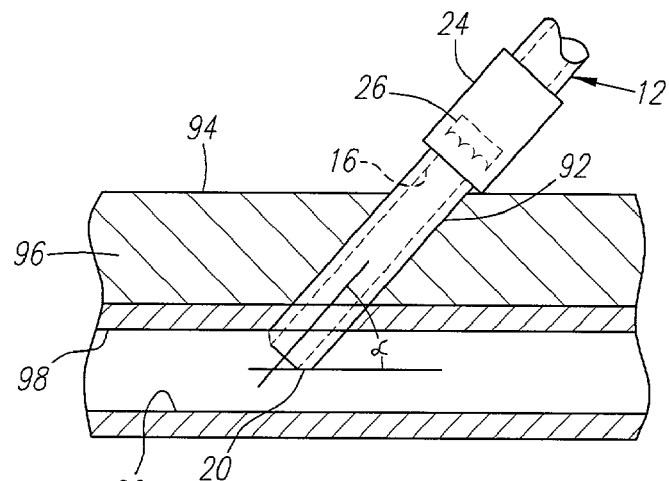

Turning now to the drawings, FIGS. 1-2 show a first preferred embodiment of an apparatus 10 for providing access into a blood vessel or other body lumen from an incision, puncture, or other passage (not shown in FIGS. 1 and 2), and/or for delivering a closure element, such as clip 26 (shown in phantom), for closing the passage. Generally, the apparatus 10 includes an introducer sheath 12, a housing 24 slidably disposed on the sheath 12, a locator member 14 insertable into the sheath 12, and an housing actuator assembly 30.

The sheath 12 includes a substantially flexible or semi-rigid tubular body 15 including a lumen 16 extending between its proximal and distal ends 18, 20. The distal end 20 has a size and shape to facilitate insertion into a blood vessel, e.g., having a tapered tip 22 for facilitating substantially atraumatic introduction through the passage and at least partially into the vessel. The lumen 16 has a size for accommodating insertion of one or more devices therethrough, such as a catheter, guidewire, and the like (not shown). The sheath 12 also preferably includes a seal (not shown), such as a hemostatic valve, within the lumen 16 at or near the proximal end 18 that provides a fluid-tight seal, yet accommodates insertion of one or more devices, such as the locator 14, into the lumen 16 without fluid passing proximally from the sheath 12.

Optionally, the sheath 12 may include a side port 19 that communicates with the lumen 16, for example, to allow the infusion of fluids into the lumen 16, through the sheath 12. Alternatively, or in addition, the side port 19 may be used to provide a "bleed back" indicator, such as that disclosed in co-pending application Ser. No. 09/680,837, filed Oct. 6, 2000, now U.S. Pat. No. 6,626,918, entitled "Apparatus and Methods for Positioning a Vascular Sheath," which is assigned to the assignee of the present invention. The disclosure of this application and any references cited therein are expressly incorporated herein.

A housing 24 is slidably disposed on an exterior of the sheath 12, the housing 24 configured for releasably holding the closure element 26. The housing 24 may include an ejector or other mechanism (not shown) for deploying the closure element 26 from the housing 24. In a preferred embodiment, the closure element 26 is an annular-shaped clip, including one or more barbs 28 for engaging the tissue around the puncture adjacent to the wall of the vessel. Preferably, the clip 26 is configured for drawing the tissue around the puncture at the wall of the vessel substantially closed and/or for enhancing hemostasis within the puncture. Exemplary embodiments of a housing and closure element for use with an apparatus in accordance with the present invention are disclosed in co-pending application Ser. Nos. 09/478,179, 09/546,998, and 09/610,238, now U.S. Pat. Nos. 6,297,042, 6,461,364, and 6,391,048, respectively, the disclosures of which are expressly incorporated herein by reference.

The housing 24 is actuable from the proximal end 18 of the sheath 12 (FIG. 1), for example, by housing actuator assembly 30, for advancing the closure element 26 distally during deployment. The housing 24 may be substantially permanently but slidably disposed on the sheath 12. In this embodiment, the housing actuator assembly 30 may be substantially permanently attached to the proximal end 18 of the sheath 12. The housing 24 may be coupled to the housing actuator assembly 30 such that the housing 24 may be directed axially along the exterior of the sheath.

Alternatively, the housing 24 may be provided separate from the sheath 12 (not shown), e.g., with the closure element 26 pre-loaded therein. In this embodiment, the housing actuator assembly 30 may also be provided separate from the sheath 12, as shown, either coupled to or separate from the housing 24. Any time before delivering the closure element 26, the housing 24 may be directed over the sheath 12, e.g., by inserting the proximal end 18 of the sheath 12. The housing actuator assembly 30 may be attached to the proximal end 18 of the sheath 12, e.g., by cooperating connectors (not shown). The housing 24 may be coupled to the housing actuator assembly 30, if not already attached, thereby preparing the housing 24 for use.

In a preferred embodiment shown in FIGS. 1 and 2, the housing actuator assembly 30 includes first and second actuator members 46, 48 that are generally movable with respect to one another. The first actuator member 46 may be connected to the proximal end 18 of the sheath 12, for example, by rods (not shown) such that the first member 46 is substantially fixed with respect to the sheath 12. A rod, cable, or other control wire 44 is coupled to and extends generally proximally from the housing 24. The control wire 44 may extend along an outer surface of the sheath 12, as shown, or alternatively may extend through a lumen (not shown) in the sheath 12 beyond the proximal end 18.

A loose end 50 of the control wire 46 may be coupled to the second actuator member 48. For example, the housing actuator assembly 30 may be advanced over the control wire 46 such that the loose end 50 passes through aperture 52 in the first member 46 and is received in a mating pocket 54 in the second member 48, as best seen in FIG. 2. The loose end 50 may be frictionally engaged within the pocket 54 or, alternatively, the loose end 50 and pocket 54 may include cooperating detents (not shown) for securing the control wire 44 to the second actuator member 48.

The second actuator member 48 may be movable with respect to the first actuator member 46 by one or more rods or rails (not shown) extending therebetween. Thus, the second actuator member 48 may be movable from a first or proximal position (not shown), located a first distance from the first actuator member 46, distally to a second or distal position (shown in FIG. 2), located a second closer distance from the first actuator member 46. When the housing actuator assembly 30 is attached to the sheath 12 with the control wire 44 coupled to the second actuator member 48, the housing 24 may be directed from a proximal position (e.g., shown in FIG. 1) to a distal or delivery position (e.g., shown in FIG. 2) when the second actuator member 48 is moved from its proximal position to its distal position.

In a preferred embodiment, the second actuator member 48 is biased to its distal position, for example, by spring 56 or other biasing element. The second actuator member 48 may be locked in its proximal position, for example, by a locking mechanism (not shown), thereby retaining the housing 24 in its proximal position. When it is desired to advance the housing 24, a button, switch, or other activation member (not shown) may be deployed to release the locking mechanism, thereby automatically directing the second actuator member 48 towards the first actuator member 46, and thereby advancing the housing 24 to its distal position, as described further below. The closure element 26 may be automatically ejected from the housing 24 once it reaches the distal position or the closure element 26 may be subsequently ejected by a separate action. It will be appreciated by those skilled in the art that other housing actuator configurations may be provided for advancing the housing 24 with respect to the sheath 12, e.g., to deliver the closure element 26.

The housing actuator assembly 30 may also include an adjustment mechanism, such as threaded bolt or knob 58. For example, the knob 58 may be provided on the first actuator member 46 such that, as the knob 58 is rotated, the first actuator member 46 may be moved axially with respect to the sheath 12. Because the first actuator member 46 may be adjusted distally or proximally with respect to the sheath 12, the distal position of the second actuator member 48 consequently may be adjusted. This, in turn, may facilitate adjusting the distal position of the housing 24, e.g., to compensate for the thickness of a particular wall of a blood vessel when a closure element 26 is delivered to close a puncture in the wall.

Turning to FIGS. 1, 2, 3A, and 3B, the locator member 14 includes a flexible or semi-rigid tubular body or other elongate rail 32 having a proximal end 34 and a distal end 36. An actuator rod or other elongate member 38 is slidably disposed with respect to the rail 32, e.g., within a lumen 33 of tubular body 32. Preferably, the locator member 14 includes an annular ridge 40 or other detent on or near its proximal end 40 that may engage a complementary-shaped pocket 42 or other cooperating detent on the sheath 12. Thus, the locator member 14 may be substantially secured axially with respect to the sheath 12.

As best seen in FIGS. 3A and 3B, a distal portion 60 of the locator member 14 includes a substantially rounded, soft, and/or flexible distal tip 62, possibly including a pigtail (not shown) that may facilitate atraumatic advancement of the distal portion 60 into a blood vessel or other body lumen. The locator member 14 preferably has a length relative to the sheath 12 such that the distal portion 60 extends beyond the distal end 20 of the sheath 12 when the locator member 14 is fully received therein, as shown in FIG. 2.

One or more, and preferably a plurality of, positioning elements 64 are provided on the distal portion 60 that may be selectively expandable between a substantially axial collapsed configuration (shown in FIG. 3A) and a substantially transverse expanded configuration (shown in FIG. 3B). Preferably, the positioning elements 64 are substantially flexible splines configured for expanding substantially transversely with respect to a longitudinal axis 13 of the apparatus 10. In one embodiment, shown in FIGS. 1 and 2, the locator member 14 includes a pair of splines 64 disposed generally opposite one another about the distal portion 60. Alternatively, as shown in FIG. 6, the locator member 14 may include four splines 64' that are substantially equally spaced about the distal portion 60. The locator member 14 may include more or fewer splines without deviating from the scope of the present invention.

Optionally, the splines 64 may include radiopaque markers (not shown) or may be at least partially formed from radiopaque material to facilitate observation of the splines 64 using fluoroscopy or other imaging systems. In addition, the housing 24 may include a radiopaque marker, e.g., at its distal end (not shown) and/or the closure element 26 may include a radiopaque marker or may be made from radiopaque material. This may facilitate monitoring the relative location of the closure element 26 to the splines 64, as described further below.

Returning to FIGS. 3A and 3B, each spline 64 preferably has a first fixed (e.g., proximal) end 64a and a second movable (e.g., distal) end 64b. The second end 64b may be axially movable towards the first end 64a to cause an intermediate region 64c of the spline 64 to expand transversely outward, thereby defining the substantially transverse expanded configuration. In a preferred embodiment, actuator rod 38 extends through the distal portion 60 and is coupled to the second end 64b of the splines 64 and/or to distal tip 62 of the locator member 14. The rod 38 may be moved axially, e.g., proximally, with respect to the rail 32 to selectively expand the splines 64 between their collapsed configuration and their expanded configuration.

A locator actuator 70 may be coupled to the locator member 14, the locator actuator 70 configured for selectively expanding the splines 64 from their collapsed configuration to their expanded configuration. For example, the locator actuator 70 may include a switch 72 that may be depressed or rotated to retract or move the rod 38 proximally, thereby expanding or deploying the splines 64. The locator actuator 70 preferably includes a lock (not shown) for securing the rod 38 in a proximal position and thereby locking the splines 64 in their expanded configuration. The lock may be released, for example, by depressing the switch 72. The locator actuator 70 may include a spring 74 or other biasing mechanism for biasing the rod 38 distally, e.g., to return the splines 64 to their collapsed configuration when the lock is released. For example, as described further below, the lock may be released upon activation of the housing actuator assembly 30, e.g., when the second actuator member 48 moves towards its distal position.

Turning to FIGS. 4A-4F, the apparatus 10 may be used to provide access into a blood vessel or other body lumen 90. Preferably, the apparatus 10 may be used to deliver a closure device, such as clip 26, to close and/or seal an incision, puncture, or other passage 92 that extends from a patient's skin 94 through intervening tissue 96, and a wall 98 of the vessel 90.

As shown in FIG. 4A, the sheath 12, without the locator member 14 therein, may be inserted or otherwise positioned within the blood vessel 90, i.e., through the passage 92. The sheath 12 is preferably provided with the housing 24 in its proximal position, without the housing actuator assembly (not shown) attached. Alternatively, the housing actuator assembly may be provided attached to the sheath 12 as long as the lumen 16 may be accessed. In a further alternative, the sheath 12 may be provided without the housing 24 thereon. The sheath 12 may be advanced over a guide wire or other rail (not shown) previously positioned through the passage 92 into the blood vessel 90 using a conventional procedure. Preferably, the blood vessel 90 is a peripheral vessel, such as a femoral or carotid artery, although other body lumens may be accessed using the sheath 12, as will be appreciated by those skilled in the art.

The passage 92, and consequently the sheath 12, may be oriented at a substantially acute angle "alpha" with respect to the vessel 90, thereby facilitating introduction of devices through the lumen 16 of the sheath 12 into the vessel 90 with minimal risk of damage to the vessel 90. One or more devices, such as a guide wire, a catheter, and the like (not shown), may be inserted through the sheath 12 and advanced to a desired location within the patient's body. For example, the devices may be used to perform a therapeutic or diagnostic procedure, such as angioplasty, atherectomy, stent implantation, and the like, within the patient's vasculature.

After the procedure is complete, the device(s) may be removed from the sheath 12, and the locator member 14 may be inserted through the hemostatic valve (not shown) into the lumen 16. If the housing 24 is not already provided on the sheath 12, the housing 24 and/or the housing actuator assembly (not shown) may be advanced over or otherwise attached to the proximal end of the sheath 12, preferably before the locator member 14 is inserted into the sheath 12.

Figure 4B:
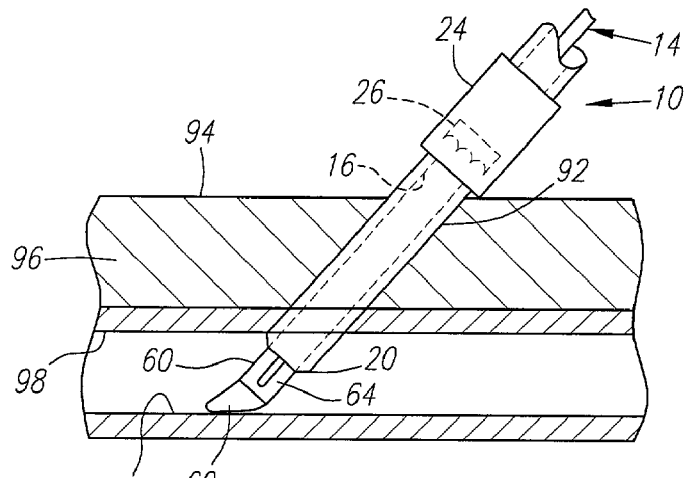

As shown in FIG. 4B, when the locator member 14 is fully inserted within the sheath 12, the distal portion 60 extends beyond the distal end 20 of the sheath 12. In an alternative embodiment, the locator member 14 may be attached to an exterior surface (not shown) of the sheath 12, for example, along a track, e.g., cooperating slots, grooves, and the like (not shown) in the sheath 12 and locator member 14. The distal tip 62 preferably is substantially soft and/or flexible such that the distal portion 60 substantially atraumatically enters the vessel 90. In this fully inserted position, cooperating detents (not shown) may be engaged to substantially secure the locator member 14 axially with respect to the sheath 12. The housing actuator assembly (not shown) may be attached to the sheath 12, e.g., by attaching a control wire (not shown) from the housing 24 to the actuator assembly, as described above.

Alternatively, the sheath 12 may include a side port (not shown) at or near its distal end 20 and a bleed back lumen (also not shown) that extends from the side port to the proximal end of the sheath 12. Before or after insertion of the locator member 14, the sheath 12 may be manipulated until "bleed back" (i.e., blood entering the side port and passing proximally through the lumen due to exposure of the side port to blood pressure within the vessel) indicates a desired position for the distal end 20 of the sheath 12. For example, the sheath 12 may be partially withdrawn from the vessel 90 before the locator member 14 is inserted into the sheath 12 to minimize contact between the vessel wall 98 and the distal portion 60 of the locator member 14 during insertion of the locator member 14 into the sheath 12.

Figure 4C:
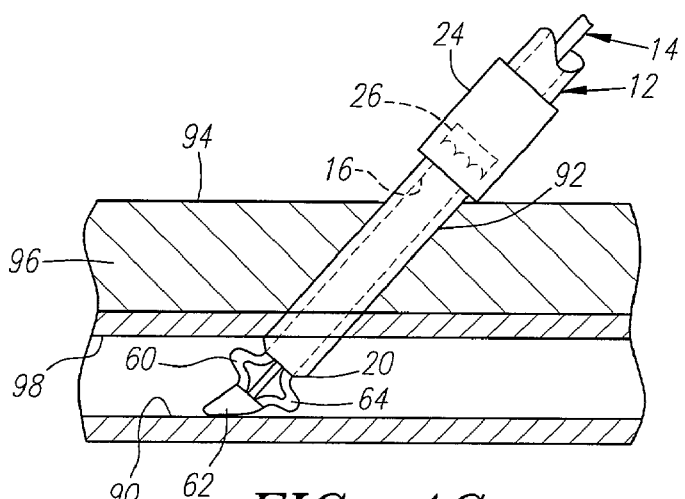
Figure 4D:
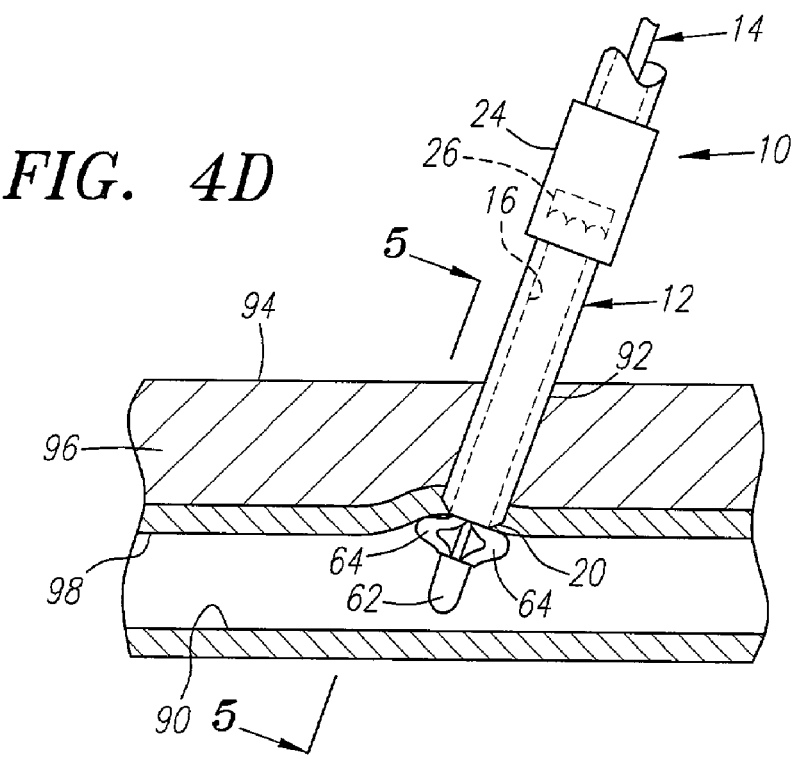

As shown in FIG. 4C, the splines 64 may then be directed to their expanded configuration, for example, by activating a switch on the proximal end (not shown) of the locator member 14. The sheath 12 and locator member 14 may then be moved in conjunction with one another, and preferably are together partially withdrawn from the vessel 90, until the splines 64 contact the wall 98 of the vessel 90, as shown in FIG. 4D. Thus, the splines 64 may provide a tactile indication of the position of the sheath 12 with respect to the wall 98 of the vessel 90. In addition, the splines 64 may assist in "presenting" the wall 98 of the vessel 90, e.g., for receiving a closure element, such as clip 26.

Figure 4E:
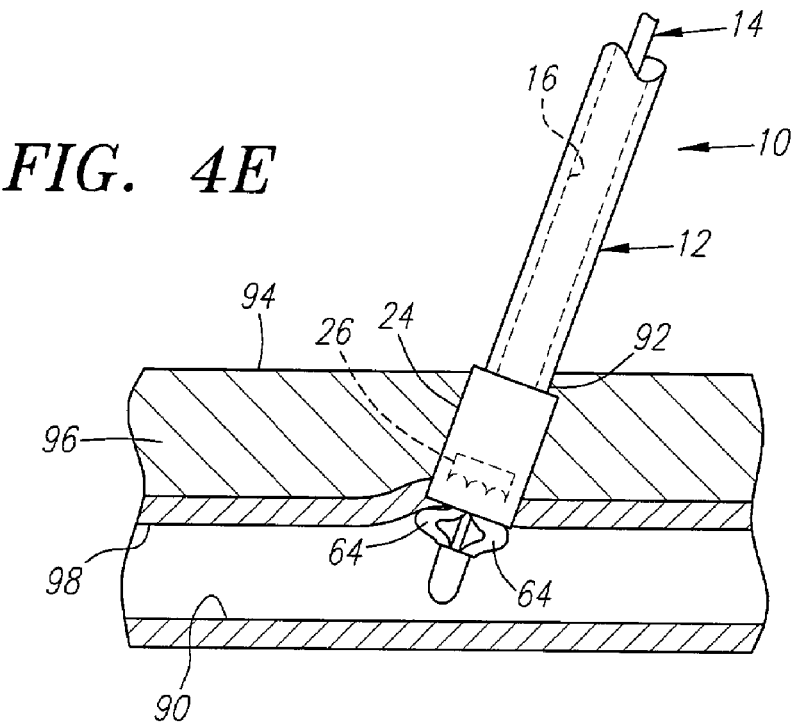

Turning to FIG. 4E, with the sheath 12 properly positioned, the housing 24 may then be actuated, for example, to advance the housing 24 distally into the passage 92 to deliver the clip 26. Preferably, movement of the housing 24 with respect to the distal end 20 of the sheath 12 is limited, e.g., by the housing actuator assembly (not shown), as described above. Preferably, the housing 24 may only be advanced a fixed distance such that the clip 26 substantially engages the wall 98 of the blood vessel, e.g., until the barbs 28 penetrate but do not pass completely through the wall 98. Thus, with the splines 64 fixed with respect to the distal end 20 of the sheath 12 and the distal position of the housing 24 fixed, the clip 26 may be advanced a predetermined distance into the passage 92 that is ascertainable and predictable. This predetermined distance may facilitate proper deployment of the clip 26 with respect to the wall 98 of the vessel 90, e.g., to prevent advancement of the clip 26 too far, i.e., into the vessel 90.

Alternatively, or in addition, the splines 64 include radiopaque markers, such that fluoroscopy and the like may be used to monitor and position the distal portion 60 of the locator member 14. The housing 24 and/or closure element 26 may also include radiopaque markers such that a relative position of the closure element 26 with respect to the splines 64, and consequently to the wall 98 of the vessel 90, may be ascertained before the closure element 26 is deployed from the housing 24.

In a preferred method, the splines 64 automatically return to their collapsed configuration when the closure element 26 is deployed from the housing 24 or when the housing 24 reaches its distal position, as shown in FIG. 4F. For example, the housing actuator assembly (not shown) may contact the locator actuator (also not shown) when the housing actuator assembly is used to advance the housing 24 to its distal position, thereby releasing the locator actuator. This enhancement may avoid any risk of contact between the clip 26 and the splines 64, e.g., which otherwise may risk driving the barbs 28 of the clip 26 through the wall 98 of the vessel 90 and into the splines 64. Alternatively, or in addition, the distal portion 60 of the locator member 14 may be automatically retracted, e.g., into the sheath 12, when the closure element 26 is deployed or the housing 24 is advanced.

Once the clip 26 is successfully deployed within the passage 92, i.e., into the wall 98 of the vessel 90, the apparatus 10 may be withdrawn from the passage 92. If the splines 64 of the locator member 14 are not automatically collapsed during advancement of the housing 24, the splines 64 may first be affirmatively collapsed, e.g., by depressing the locator actuator (not shown). The entire apparatus 10 may then be removed in one step, or alternatively, the locator member 14 may first be withdrawn from the sheath 12 before withdrawing the sheath 12, thereby leaving the clip 26 in place to close and/or seal the passage 92.

Turning to FIGS. 7A and 7B, another embodiment of a distal portion 160 of a locator member 114 is shown that may be used to position a sheath (not shown) before delivering a closure element (also not shown), similar to the embodiment described above. The locator member 114 includes a flexible or semi-rigid tubular body 132 having a proximal end (not shown) and a distal end 136. An actuator wire or rod 138 is slidably disposed with respect to the body 132, e.g., within a lumen 133 of body 132. The locator member 114 may include a detent (not shown) on or near its proximal end for securing the locator member 114 to a sheath (not shown).

The locator member 114 includes a distal portion 160 that terminates in a substantially rounded, soft, and/or flexible distal tip 162, possibly including a pigtail (not shown) that may facilitate atraumatic advancement of the distal portion 160 into a blood vessel or other body lumen. The locator member 114 preferably has a length relative to the sheath such that the distal portion 160 extends beyond a distal end of the sheath when the locator member 114 is fully received in the sheath, similar to the embodiment described above.

A plurality of splines 164 are provided on the distal portion 160 that may be selectively expandable between a substantially collapsed configuration (shown in FIG. 7A) and a substantially transverse expanded configuration (shown in FIG. 7B). Preferably, the splines 164 are substantially rigid or semi-rigid elements that include hinged regions 166, 168 that facilitate expansion substantially transversely with respect to a longitudinal axis 113 of the locator member 114. In one embodiment, each spline 164 is a single piece that includes a plurality of living hinges 166, 168. Alternatively, each spline 164 may include multiple segments that are connected by pins or other hinges (not shown). In a preferred embodiment, the distal portion 160 includes -four equally spaced splines 164, although the locator member 14 may include more or fewer splines without deviating from the scope of the present invention. Optionally, the splines 164 may include radiopaque markers (not shown), similar to the embodiment described above.

Each spline 164 preferably has a first fixed end 164a and a second movable end 164b. The second end 164b may be axially movable towards the first end 164a to cause an intermediate region 164c of the spline 64 to expand transversely outward, thereby defining the substantially transverse expanded configuration. In a preferred embodiment, the actuator rod 138 extends through the distal portion 160 and is coupled to the second end 164b of the splines 164 and/or to distal tip 162 of the locator member 114. The rod 138 may be moved axially with respect to the body 132 to selectively expand the splines 164 between the collapsed and expanded configurations.

Turning to FIG. 8A, a locator actuator 170 may be coupled to the control rod 138 and a proximal end 134 of the locator member 114. The locator actuator 170 is configured for directing the control rod 138 axially to selectively expand the splines 164, similar to the embodiment described above.

In addition, the locator actuator 170 may allow the splines 164 to be expanded to one of a plurality of expanded configurations. For example, the locator actuator 170 may include an internal member (not shown), coupled to the control rod 138, that is slidable within an actuator body 176. A button 172 extending from the internal member is slidable in an axial slot 174 in the actuator body 176 for controlling movement of the control rod 138. The button 172 may be moved, thereby moving the control rod 138 and consequently moving the splines 164. For example, as shown in FIG. 8A, the button 172 may be moved to a position (for example, indicated as "4"thereby expanding the splines 164 to an expanded diameter 165a. If desired, the button 172 may be moved to other available positions to reduce the expanded diameter, for example to the diameter 165b shown in FIG. 8B. This control of the expanded diameter of the splines 164 may be useful to allow the splines 164 to be deployed within body lumens of different sizes. Thus, the splines 164 may be expanded to a desired size corresponding to the size of the vessel into which the locator 114 is introduced, thereby minimizing the risk of damage to the vessel due to over expansion of the splines 164.

In an alternative embodiment, shown in FIG. 8B, the locator actuator 170' may include a rotatable dial that controls expansion of the splines 164, similar to the linear actuator 170 shown in FIG. 8A. In addition, the locator actuator 170, 170' may include demarcations indicating a size (not shown), e.g., a diameter of the expanded splines and/or the size of the body lumen corresponding to the size of the lumen into which the locator 114 is to be introduced.

Figure 9:
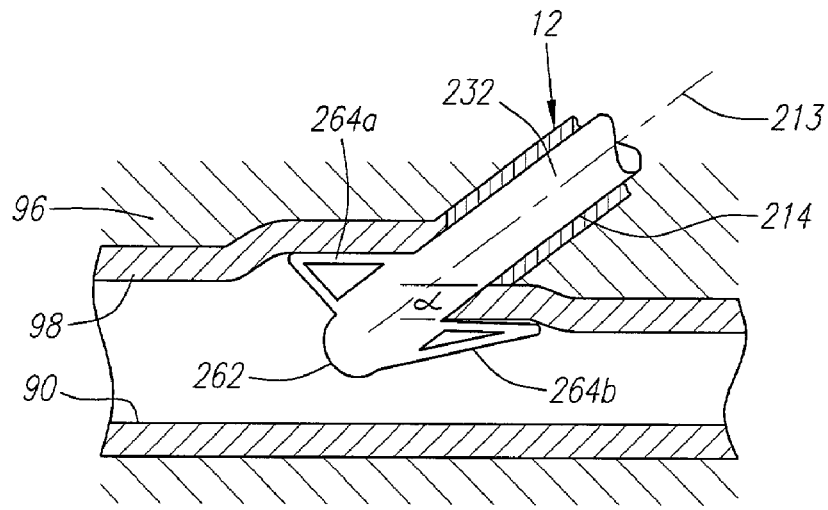
FIG. 9 is a cross-section view of a distal portion of an alternative embodiment of an apparatus for delivering a closure element, in accordance with the present invention.

In a further alternative shown in FIG. 9, a locator member 214 may be provided that includes splines 264 tha may be selectively expanded to different angles. A locator actuator (noy shown) may allow controlled expansion of the splines 264a, 264b desired angles with respect to the longitudinal axis 213 of the locator member. For example, a cable or other control wire (not shown) may be extended from the locator actuator to each of the splines 254a, 264b, e.g., through a lumen (not shown) in the locator body 232. Each cable may be directed axially to selectively expand or collapse the spline 264a, 264b connected to the respective cable.

For example, a spline 264b on the posterior side of the locator member 214 (away from the surface of the patient's skin) may be expanded towards the proximal end of the locator member 214 at an acute angle "alpha," i.e., corresponding substantially to the angle of the passage through the patient's skin to the vessel 90, e.g., about thirty or forty five degrees. In contrast, the spline 264a on the anterior side of the locator member 214 (i.e. towards the surface of the patient's skin) may be expanded away from the proximal end of the locator member 214 at an oblique angle of one hundred eighty degrees less "alpha." Thus, the splines 264 may be expanded to predetermined angles that facilitate better contact with the wall of the vessel, e.g., to better "present" the vessel wall during deployment of a closure element.

Figure 10:
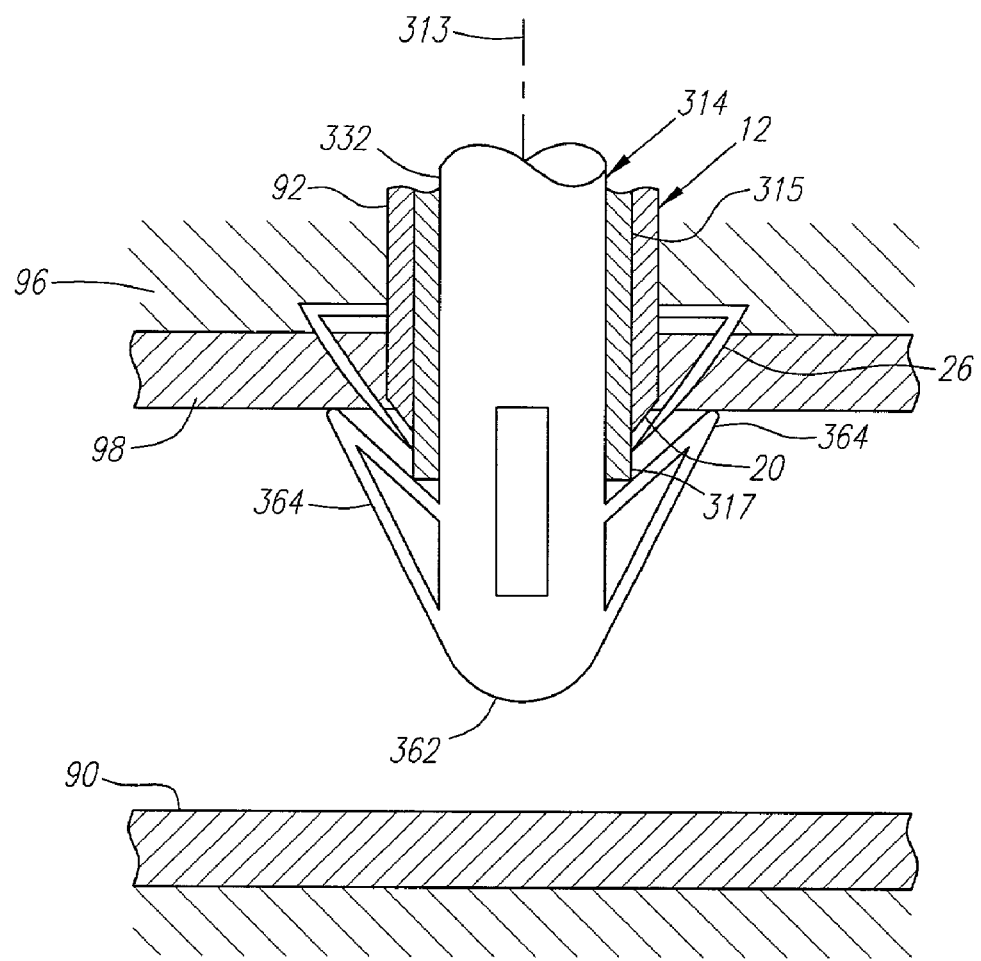
FIG. 10 is a cross-sectional view of a distal portion of yet another alternative embodiment of an apparatus for delivering a closure element, in accordance with the present invention.

In yet another alternative embodiment, shown in FIG. 10, a locator member 314, such as those described above, may include a tubular sleeve 315 within which a body 332, including splines 364, may be axially directed. For example, a proximal end (not shown) of the sleeve 315 may be fixed to a proximal end (also not shown) of the body 332, e.g., to a locator actuator (not shown), such as those described above. At least a distal portion 317 of the sleeve 315 is formed from a substantially rigid, smooth walled tube, such as a hypotube, while the remainder of the sleeve 315 may be a portion of the same tube or may be formed from a substantially flexible or semi-rigid tubular member (not shown).

When the locator member 314 is fully inserted into an introducer sheath 12, such as those described above, the distal portion 317 of the sleeve 315 extends beyond a distal end 20 of the sheath 12. The splines 364 may then be selectively deployed from within the sleeve 315, expanded to a substantially transverse expanded configuration, collapsed, and retracted back into the sleeve 315.

For example, the sheath 20 may be positioned through a puncture 92 into a vessel 90, e.g., to perform a procedure within a patient's vasculature, as described above. The locator member 314 may then be inserted into the sheath 12 until the distal portion 317 extends beyond the distal end 20 of the sheath 12. The splines 364 may then be expanded, and the sheath 12 and locator member 314 manipulated to a desired position, e.g., such that the splines 364 contact the wall 98 of the vessel 90, thereby providing a tactile indication of the position of the sheath 12.

A closure element, such as clip 26 may then be deployed, e.g., from a housing (not shown) slidably mounted on the sheath 12. Barbs or tines 28 on the clip 26 penetrate into the wall 98 of the vessel 90, e.g., to close the opening in the wall 98 of the vessel 90, as described above. If the barbs 28 penetrate completely through the wall 98 of the vessel 90, the sleeve 315 protects the splines 364 and/or the body 33 of the locator member 314. The barbs 28 may engage but not penetrate or otherwise catch on the distal portion 317 of the sleeve 315, because of its substantially rigid and/or smooth construction. Thus, the barbs 28 may not penetrate or otherwise catch on the splines 364 when the clip 26 is deployed. The splines 364 may be collapsed and retracted into the sleeve 315, either manually or automatically, similar to the embodiments described above. When the sheath 12 is withdrawn from the puncture 92, the barbs 28 may slide along the distal portion 317 of the sleeve 315 until the distal portion 317 is withdrawn from within the clip 26, whereupon the barbs 28 may move inwards to close and/or seal the opening in the wall 98 of the vessel 90.

In alternative embodiments, the apparatus and methods of the present invention may be used to locate an introducer sheath within a blood vessel and/or to deliver closure elements other than a clip. For example, the apparatus may be used to deliver a collagen plug and the like into the passage, or a sealing material (either alone, or in conjunction with a clip).

Turning to FIGS. 11A-12B, another preferred embodiment of an apparatus 410 is shown for sealing a passage through tissue communicating with a body lumen, such as a blood vessel, in accordance with the present invention. Generally, the apparatus 410 includes a plug member 412, an elongate shaft or handle device 414, and a locator member 416.

With particular reference to FIGS. 11A and 11B, the locator member 416 includes a helically wound wire 444 that includes proximal and distal ends 446, 448, defining a longitudinal axis 438 therebetween. The helically wound wire 444 may be formed from flexible material that is biased to assume an axial configuration, as shown in FIG. 11A, but may be deflectable, e.g., by buckling, as explained further below. The helically wound wire 444 has a diameter such that the locator member 416 may be advanced through a lumen 440 of the handle device 414 (as shown in FIGS. 12A and 12B) and/or directly into a passage through tissue. Preferably, adjacent turns of the helically wound wire 444 are in close proximity to or substantially abut one another in a relaxed state free from external forces, yet may be slidable and/or bendable with respect to one another to facilitate buckling of the locator member 416. Alternatively, adjacent turns of the helically wound wire 444 may have spaces between them in the relaxed state.

In a further alternative, the helically wound wire 444 may extend only partially from the distal end 448 towards the proximal end 446 (not shown). In this alternative, the locator member 416 may include a substantially straight wire, tubular body, or other proximal portion (not shown) that may extend from the helically wound wire to the proximal end 446 of the locator member 416. The proximal portion may be relatively more rigid, e.g., resistant to buckling than the helically wound wire and/or may be supported by the wall of the lumen 440 of the handle device 414.

The locator member 416 also includes a tether or other control element 450 that is coupled to the helically wound wire 444. Preferably, the tether 450 is an elongate wire, ribbon, cable, and the like that has a distal end 452 that is coupled to the distal end 448 of the helically wound wire 444. The tether 450 may include a handle 456 on its proximal end 458 for selectively pulling the tether 450 in a proximal direction to cause the helically wound wire 444 wire to buckle, as explained further below.

The tether 450 may extend along an outer surface of the helically wound wire 444 at least partially from the distal end 448 towards the proximal end 446, thereby defining a deflectable distal portion 454. For example, the tether 450 may extend along the outer surface of the helically wound wire 444 along its entire length. Alternatively, the tether 450 may extend along the outer surface of the distal portion 454, and then may pass between turns of the helically wound wire 444, and extend within the helically wound wire 444 to the proximal end 446 of the locator member 416. In a further alternative, the tether 450 may extend its entire length within the helically wound wire 444. For example, if the helically wound wire 444 has gaps between adjacent turns, the helically wound wire 444 may be compressed when the tether 450 is pulled to cause the helically wound wire 444 to buckle.

An actuator (not shown) may be provided on the proximal end 446 of the locator member 416. The actuator may be coupled to the proximal end 458 of the tether 450 and to the helically wound wire 444 for providing controlled relative movement of the tether 450 and the helically wound wire 444, as will be appreciated by those skilled in the art.

When the proximal end of the tether 450 is in its distal-most position, the helically wound wire 444 may extend generally parallel to the longitudinal axis 438, thereby defining an axial or inactivated configuration, such as that shown in FIG. 11A. Even if the distal portion of the helically wound wire 448 becomes slightly curved, e.g., when inserted into a body lumen, the distal portion is still considered "generally parallel" to the longitudinal axis 438. When the tether 450 is directed proximally, e.g., by applying a proximal force on the proximal end 458 and/or handle 456, it may pull the distal end 448 of the helically would wire 444 towards the proximal end 446, thereby causing the distal portion 454 of the helically wound wire 444 to buckle, thereby assuming a transverse or activated configuration, such as that shown in FIG. 11B.

Turning to FIGS. 12A and 12B, the plug member 412 is a body, preferably having a generally cylindrical shape, including a proximal end 420, a distal end 422, and an outer surface 430. The plug member 412 includes a lumen 424 that extends between a proximal opening 426 and a distal opening or port 428. The plug member 412 may be formed from biocompatible material, and preferably from bioabsorbable material, and/or may be substantially rigid or partially flexible.

The plug member 412 generally includes a helical thread pattern 418, including one or more helical threads, that extends at least partially between its proximal and distal ends 420, 422. The helical thread pattern 418 is preferably substantially rigid and may have a substantially square cross-section to facilitate sealing of a passage into which the plug member 412 is threaded.

A sealing member (not shown) may be provided within the lumen 424 for substantially sealing the lumen 424 from fluid flow therethrough. The sealing member is preferably formed from a material that expands when exposed to fluids, e.g., a gel foam, and may be bioabsorbable, e.g., if the plug member 414 is. Before exposure to fluid, the sealing member may be substantially recessed from the lumen 424, thereby accommodating inserting devices therethrough. Upon exposure to fluid, e.g., blood, the sealing member may expand, e.g., due to hydration and the like, across the lumen 424 and/or otherwise substantially seal the lumen 424.

Alternatively, the sealing member may be a valve (not shown) or a coil of material that is biased to substantially seal the lumen 424 from fluid flow. For example, the sealing member may be biased to substantially seal the lumen 424, yet may be deflected to accommodate insertion of one or more devices therethrough. In a further alternative, the lumen 424 may have a relatively small cross-section, and the sealing member may be omitted.

Additional information regarding plug members appropriate for use with the present invention may be found in U.S. Pat. No. 5,292,332 to Lee and U.S. Pat. No. 5,290,310 to Makower et al., the disclosures of which are expressly incorporated herein by reference.

Returning to FIGS. 12A and 12B, the handle device 414 has a proximal end 434, a distal end 436, and a lumen 440 that extends between the proximal and distal ends 434, 436, e.g., for accommodating insertion of the locator member 416 and/or other devices therethrough. A handle 442 may be provided on the proximal end 434 of the shaft 414 for facilitating manipulation of the apparatus 410, e.g., to facilitate rotation of the apparatus 410 into a passage, as described below. Preferably, the handle device 414 is a substantially rigid tubular member having a cross-section that is substantially smaller than a cross-section of the plug member 412, e.g., to minimize dilation of a passage into which the plug member 412 is inserted.

The plug member 412 and the distal end 436 of the handle device 414 generally include one or more connectors (not shown) for releasably securing the plug member 412 to the handle device 414, as described in application Ser. No. 09/732,835, filed Dec. 7, 2000, the disclosure of which is expressly incorporated herein by reference. Preferably, cooperating connectors (not shown) substantially couple the plug member 412 to the handle device 414 such that the plug member 412 cannot move independently of the handle device 414, e.g., such that the plug member 412 may be rotated only by rotating the handle device 414. Preferably, the handle 442 includes an actuator (not shown) that may be activated to release the connectors securing the plug member 412 to the handle device 414.

When the locator member 416 is fully inserted into the handle device 414, the distal portion 454 of the locator member 416, is preferably disposed beyond the distal end 436 of the handle device 414, and, more preferably, beyond the distal end 422 of the plug member 412, as shown in FIG. 12B. The locator member 416 may be coupled to the handle device 414, e.g., by cooperating detents or other connectors on their respective proximal ends 446, 434. All of the distal portion 454 of the locator member 416 may be disposed beyond the distal end 422 of the plug member 412, or a portion of the distal portion 454 may extend into the lumen 424 of the plug member and/or the lumen 440 of the handle device 414.

Figure 13D:
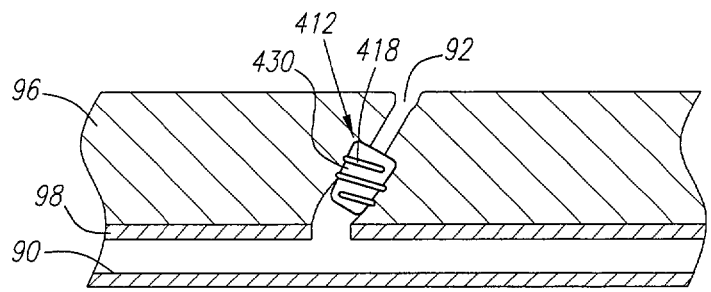
Figure 14:
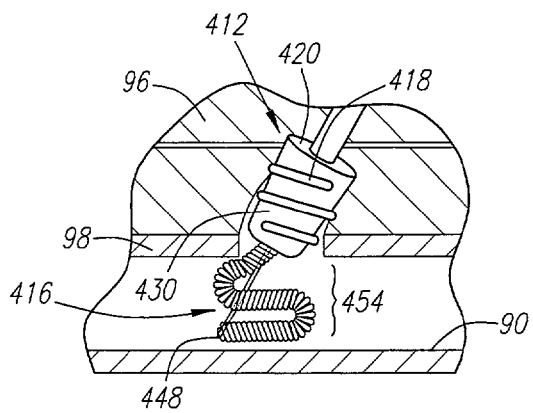
FIG. 14 is a detail of FIG.

Turning to FIGS. 13A-13D, during use, the apparatus 410 may be used to seal and/or close a passage through tissue 96, such as a puncture 92 communicating with a blood vessel 90 or other body lumen. Initially, the plug member 412 may be connected to or otherwise disposed on the handle device 414. The locator device 416 may be inserted into the handle device 414 until the distal portion 454 extends beyond the plug member 412, as shown in FIG. 12B (but with the distal portion 454 in its axial configuration as shown in FIGS. 13A and 13B).

The puncture 92 may be used to provide percutaneous access to the vessel 90. For example, the puncture 92 may facilitate performing an endovascular procedure within a patient's vasculature, such as angioplasty, stenting, atherectomy, and the like, or may otherwise provide access via the vessel 90 to a region within the patient's body. Upon completion of the procedure, any instruments, such as an introducer sheath (not shown), may be removed from the vessel 90 and puncture 92.

The apparatus 410 may then be introduced into the puncture 92, for example, by initially inserting the distal portion 454 of the locator member 416 into the puncture 92. The distal portion 454 may have a substantially atraumatic distal tip, e.g., tapered and/or relatively flexible, to facilitate advancement of the apparatus 410 into the puncture 92. As the distal portion 454 of the locator member 416 is advanced into the puncture 92, the plug member 412 may be inserted into the puncture 92, as shown in FIG. 13A.

Because of the thread pattern 418, the handle device 414 may be rotated in a first direction to thread the plug member 412 into the puncture 92. Consequently, the outer surface 430 and/or the thread pattern 418 may engage tissue 96 surrounding the puncture 92, thereby substantially sealing the puncture 92 from fluid flow, such as blood flow, within the vessel 90. The apparatus 410 may be rotated in the first direction about its longitudinal axis 438 to thread the plug member 412 substantially atraumatically deeper into the puncture 92.

Turning to FIG. 13B, as the plug member 412 is advanced, the distal portion 454 of the locator device 416 eventually passes through the wall 98 of the vessel 90. This advancement may be monitored by providing one or more radiopaque markers (not shown) and the like on the handle device 414, the plug member 412, and/or the locator member 416, and using fluoroscopy while advancing the apparatus 410. Alternatively, depth markers (not shown) may be provided on the exterior of the handle device 414 for visual monitoring advancement. Tactile indication, e.g., resistance to further advancement, may also identify that the vessel 90 has been attained.

Once it is confirmed that the distal portion 454 is located within the lumen 90, the locator member 416 may be activated, e.g., by pulling the handle 456 proximally or activating an actuator (not shown) at the proximal end of the locator member 416. This causes the distal portion 454 to buckle to its transverse configuration, as shown in FIG. 13C. In the transverse configuration, the distal portion 454 has a cross-section such that the distal portion 454 may not be withdrawn into the plug member 412 and/or the puncture 92.

Rotation of the apparatus 410 may then be reversed, i.e., in a second direction opposite the first direction, to withdraw the plug member 412 a predetermined distance relative to the vessel 90. As the plug member 412 is withdrawn, the distal portion 454 of the locator member 416 may engage a wall 98 of the vessel 90, thereby creating resistance to further rotation. This may provide tactile feedback that the plug member 412 is disposed at a desired location, e.g., within the puncture 92 in close proximity to the vessel 90, but not extended into the vessel 90.

The plug member 412 may then be released from the handle device 414. The locator member 416 may be deactivated, i.e., returned to its axial configuration, and then withdrawn from the plug member 412, either simultaneously with withdrawal of the handle device 414 or before withdrawal of the handle device 414. The sealing member (not shown) preferably substantially seals the lumen 424 (not shown, see FIGS. 12A and 12B) within the plug member 412 to prevent fluid within the vessel 90 from passing therethrough to leak from the puncture 92. Alternatively, leakage through the lumen 424 may be sufficiently insignificant, e.g., hemostatis may occur rapidly despite the presence of the lumen 424, and the sealing member may be eliminated.

Preferably, as explained above, the sealing member is a material that expands when exposed to fluid. For example, as the locator member 416 is withdrawn (either before or along with the handle device 414), fluid, e.g., blood, may flow proximally through the lumen 424 in the plug member 412, e.g., until it encounters the sealing member. Although a relatively small amount of fluid may pass beyond the sealing member, the sealing member may expand substantially due to the fluid contact until it substantially seals the lumen. Alternatively, the sealing member may be a valve that may open to accommodate the locator member 416, but may automatically close upon withdrawal of the locator member 416.

If the plug member 412 is bioabsorbable, it may remain within the puncture 92 as the tissue heals, thereby allowing the wall 98 of the vessel 90 and tissue 96 surrounding the passage 92 to at least partially heal before the plug member 12 is absorbed. Alternatively, the plug member 412 may be retrieved once the tissue between the plug member 12 and the vessel 90 has substantially healed.

In an alternative embodiment, a guidewire 102 may be used during the procedure. The apparatus 410 may be provided initially without the locator member 416, and the guidewire 102 may be backloaded through the plug member 412 and handle device 414. The guidewire 102 may be used to guide the plug member 412 as it is threaded through the puncture 92 until it at least partially enters the vessel 90. Once the vessel 90 has been attained, the guidewire 102 may be withdrawn, and the locator member 416 may be inserted through the handle device 414 until the distal portion 454 extends beyond the plug member 412 into the vessel 90. The distal portion 454 may be activated, and then the procedure may proceed substantially as just described to deliver the plug member 412.

In a further alternative, the locator member 416 shown in FIGS. 11A and 11B may be used to position and/or deliver other closure elements. For example, the locator member 416 may be substituted for the locator member with expandable positioning elements shown and described above in connection with FIGS. 1-3B, e.g., to deliver a clip within a housing that is slidable along a sheath (not shown) through which the locator member 416 may be inserted. In yet another alternative, the locator member with expandable positioning elements shown and described above in connection with FIGS. 1-3B may be used in place of the locator member 416 to position and/or deliver the plug member 412, using methods similar to those described above.

Turning to FIGS. 15A-15D, an apparatus 410 may be used in conjunction with an introducer sheath 402 or other tubular member already in place within the passage 92. For example, the introducer sheath 402 may be used to access the vessel 90 to perform a procedure within the patient's vasculature or elsewhere within the patient's body, as described above. The sheath 402 may be disposed such that a proximal end 404 is located outside the passage 92, and a distal end 406 is located within the vessel 90.

Figure 15A:
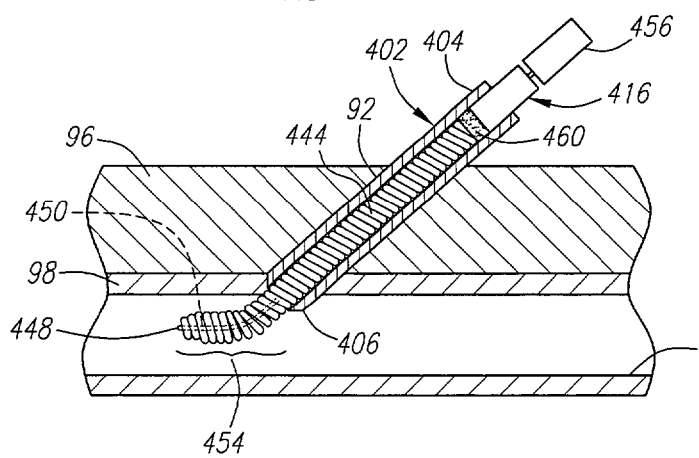
FIGS. 15A-15D are cross-sectional side views, showing another method for delivering a plug member using the apparatus of FIGS. 12A and 12B.
Figure 15B:
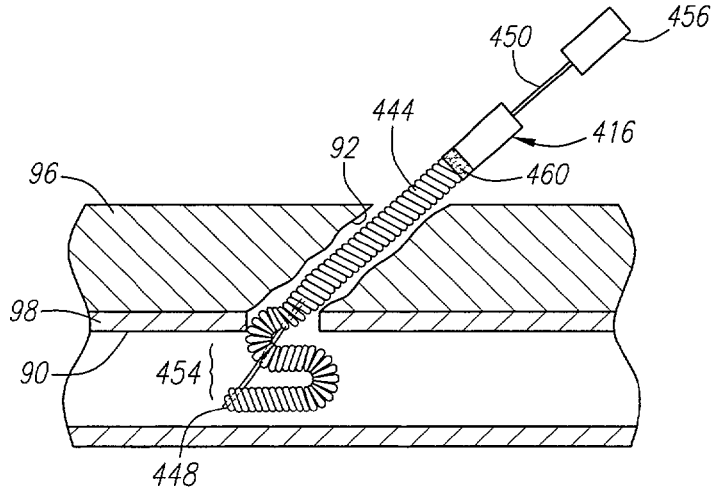
Figure 15C:
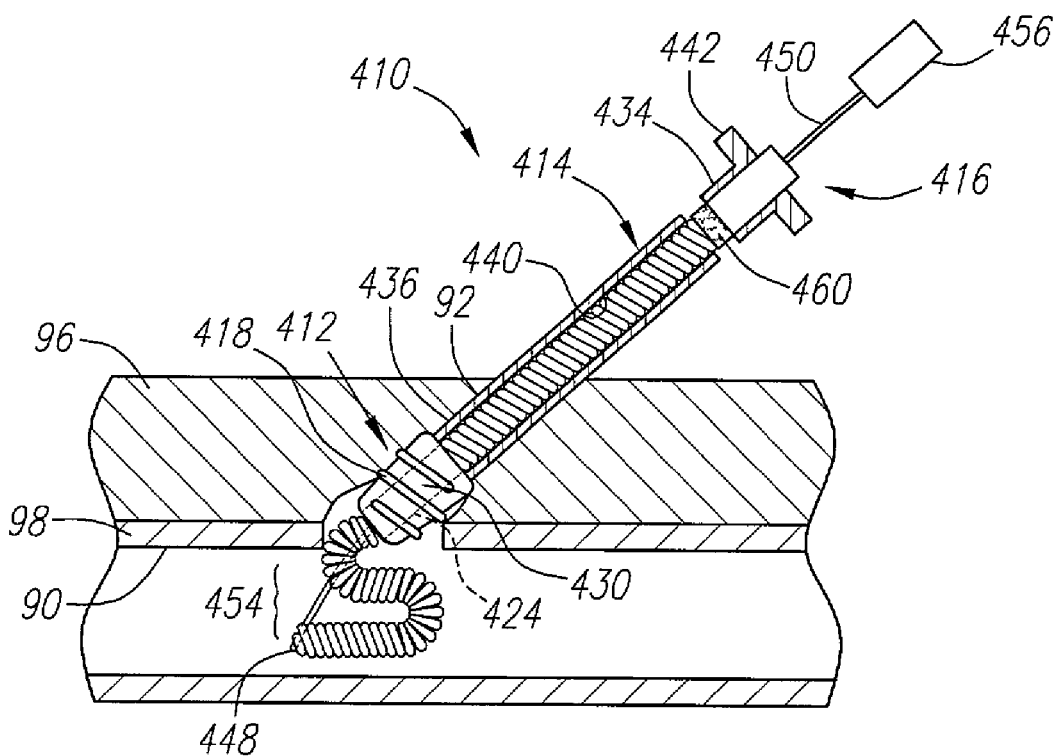
Figure 15D:
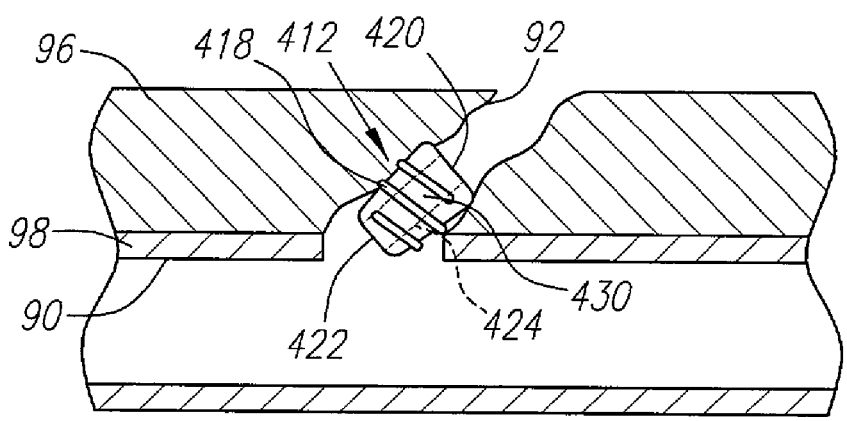

As shown in FIG. 15A, the locator member 416 may be inserted through the introducer sheath 402 until the distal portion 454 extends beyond the distal end 406 of the sheath 402 into the vessel 90. The distal portion 454 may be buckled from the axial configuration to the transverse configuration, as described above, and then the locator member 416 may be manipulated, e.g., pulled proximally, such that the buckled distal portion 454 engages or otherwise contacts a proximal wall 92 of the vessel 90. Thus, the locator member 416 may be secured from proximal movement relative to the vessel 90 and/or may provide tactile feedback of the location of the distal portion 416. The sheath 402 may be removed from the passage 92 either before or after buckling the distal portion 454 of the locator member 416.

The plug member 412 may then be advanced over the locator 416 member into the passage 92. For example, the plug member 412, disposed on the distal end 436 of an elongate member 414, may be threaded through the tissue 96 along the passage 92 such that threads 418 on the plug member 412 substantially engage the surrounding tissue 96. The locator member 416 may pass through a passage 424 in the plug member 412 and/or through the lumen 440 of the elongate member 414. Once the plug member 412 reaches a desired location within the passage 92, the plug member 412 may be released from the distal end 436 of the elongate member 414.

To facilitate positioning of the plug member 412 relative to the vessel 90, the locator member 416 and/or the elongate member 414 may include one or more depth markers. For example, the locator member 416 may include a marker band 460 at a predetermined location relative to the distal portion 454. The elongate member 414 may include a window 462 or other opening at a predetermined location on its proximal end 434. When the marker band 460 on the locator member 416 appears in the window 462, it may provide a visual indication that the plug 412 is disposed at a predetermined position relative to the wall 98 of the vessel 90. Alternatively, the locator member 416 and the elongate member 414 may include other cooperating elements, e.g., cooperating tactile elements as described above, for identifying when the plug 412 is disposed at a predetermined location.

After the plug 412 is released from the elongate member 414, the distal portion 454 of the locator member 416 may be returned to its axial configuration, and the elongate member 414 and the locator member 416 may be withdrawn from the passage 92, leaving the plug member 412 to substantially seal the passage 92, similar to the embodiments described above.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for positioning a closure device within a passage, comprising:
   an elongate member comprising a proximal end, a distal end, and a lumen extending between the proximal and distal ends defining a longitudinal axis;
   a clip deliverable from the elongate member for sealing the passage; and
   a selectively expandable locator member extending through the lumen, the locator member comprising a distal portion extending distally beyond the distal end of the elongate member, the distal portion comprising an elongate deflectable element comprising a helically wound wire extending between a proximal end and a distal end, and having an intermediate portion therebetween, and a control element fixedly connected to the distal portion of the deflectable element and extending along an outer surface of at least one coil of the helical wound wire and passing through at least one coil of the helical wound wire in a pre-deployed configuration, the control element extending from the distal portion to the proximal end of the expandable locator member and being movable axially to buckle an intermediate portion of the deflectable element substantially transversely with respect to the longitudinal axis.

2. The apparatus of claim 1, wherein the control element comprises a tether extending along an outer surface of at least the intermediate portion of the helically wound wire.

3. The apparatus of claim 2, wherein the intermediate portion of the deflectable element has a cross-section in its buckled configuration that is larger than a cross-section of the distal portion.

4. The apparatus of claim 1, further comprising an actuator on a proximal end of the elongate member, the actuator coupled to the locator member, the actuator configured for moving the control element proximally for buckling the intermediate portion of the deflectable element.

5. The apparatus of claim 1, wherein the elongate member and the selectively expandable locator member comprise cooperating detents for substantially securing the selectively expandable locator member axially with respect to the elongate member when the selectively expandable locator member is fully inserted into the elongate member.

6. The apparatus of claim 1, further comprising a housing slidably disposed on an exterior of the elongate member, the housing configured for releasably holding the clip, the housing being actuable for advancing the clip distally towards the distal end of the elongate member for deploying the clip.

7. An apparatus for delivering a closure element into a passage communicating with an opening into a body lumen, comprising:
   an elongate member comprising proximal and distal ends and defining a longitudinal axis;
   a housing slidably coupled to the elongate member, the housing configured for releasably holding a closure element, the closure element comprising a clip; and
   a locator member coupled to the elongate member, the locator member having a distal portion extending distally beyond the distal end of the elongate member, the distal portion comprising helically wound wire comprising a proximal end, a distal end, and an intermediate portion therebetween, and a control element fixedly connected to the distal end of the helically wound wire, the control element extending from the distal portion to the proximal end of the expandable locator member and between a first pair of adjacent uniform coils of the helical wound wire and along an outer surface of at least one coil of the helical wound wire and passing between a second pair of adjacent uniform coils of the helical wound wire in a pre-deployed configuration and being movable axially to buckle the intermediate portion of the helically wound wire substantially transversely with respect to the longitudinal axis.

8. The apparatus of claim 7, wherein the control element comprises a tether extending along an outer surface of at least the intermediate portion of the helically wound wire.

9. The apparatus of claim 7, wherein the elongate member and the locator member include cooperating detents for substantially securing the locator member axially with respect to the elongate member.

10. The apparatus of claim 7, further comprising an actuator coupled to the housing, the actuator configured for advancing the housing distally to deploy the closure element therefrom.

11. The apparatus of claim 7, further comprising the closure element located within the housing.

12. The apparatus of claim 7, wherein at least a portion of the helically wound wire is configured to communicate with the body lumen.

13. An apparatus for positioning a closure device within a passage through tissue communicating with a body lumen, comprising:
   an elongate member comprising a proximal end, a distal end, and a lumen extending between the proximal and distal ends defining a longitudinal axis;
   a clip deliverable from the elongate member for sealing the passage; and
   a locator member extending through the lumen, the locator member comprising a distal portion extending distally beyond the distal end of the elongate member, the distal portion comprising an elongate deflectable element comprising a proximal end and a distal end, and a control element fixedly connected to a distal portion of the deflectable element, the control element extending from the distal portion to the proximal end of the locator member and being moveable axially to buckle an intermediate portion of the deflectable element substantially transversely with respect to the longitudinal axis wherein the deflectable element comprises a helically wound wire extending between the proximal and distal ends of the deflectable element and having an intermediate portion therebetween, and wherein the control element comprises a tether extending along an outer surface of at least the intermediate portion of the helically wound wire in a pre-deployed configuration.

14. The apparatus of claim 13, wherein the intermediate portion of the deflectable element has a cross-section in its buckled configuration that is larger than a cross-section of the distal portion.

15. The apparatus of claim 13, further comprising an actuator on a proximal end of the elongate member, the actuator coupled to the locator member, the actuator configured for moving the control element proximally for buckling the intermediate portion of the deflectable element.

16. The apparatus of claim 13, wherein the elongate member and the locator member comprise cooperating detents for substantially securing the locator member axially with respect to the elongate member when the locator member is fully inserted into the elongate member.

17. The apparatus of claim 13, further comprising a housing slidably disposed on an exterior of the elongate member, the housing configured for releasably holding the clip, the housing being actuable for advancing the clip distally towards the distal end of the elongate member for deploying the clip.

18. The apparatus of claim 13, wherein at least a portion of the helically wound wire is configured to communicate with the body lumen.

19. A method for sealing a passage communicating with a body lumen using an elongate member comprising proximal and distal ends, and a closure element deployable from the distal end of the elongate member, the method comprising:
   providing a selectively expandable locator member coupled to the elongate member such that a distal portion of the locator member extends distally beyond the distal end of the elongate member;
   advancing the distal end of the elongate member through a patient's skin towards the body lumen via the passage until the distal portion of the locator member is located within the body lumen;
   moving a control element fixedly connected to a distal end of the deflectable element to buckle the deflectable element on the distal portion of the selectively expandable locator member from an axial collapsed configuration to a transverse expanded configuration, the deflectable element comprising a helically wound wire extending between a proximal end and a distal end and having an intermediate portion therebetween and the control element extending from the distal portion to the proximal end of the expandable locator member and extending along an outer surface of at least one coil of the helical wound wire and passing through at least one coil of the helical wound wire in a pre-deployed configuration;

manipulating the elongate member until the deflectable element in the expanded configuration contacts a proximal wall of the body lumen, thereby providing a tactile indication of a location of the distal end of the elongate member relative to the body lumen; and deploying the closure element from the distal end of the elongate member within the passage, the closure element comprising a clip.

20. The method of claim 19, further comprising withdrawing the elongate member and the selectively expandable locator member from the passage, leaving the closure element to substantially close the opening.

21. The method of claim 19, wherein the elongate member comprises an introducer sheath, and wherein the method further comprises introducing one or more instruments through the lumen of the sheath into the body lumen prior to performing the steps of:

providing a selectively expandable locator member coupled to the elongate member such that the distal portion of the locator member extends distally beyond the distal end of the elongate member;

advancing the distal end of the elongate member through the patient's skin towards the body lumen via the passage until the distal portion of the locator member is located within the body lumen;

buckling the deflectable element on the distal portion of the selectively expandable locator member from the axial collapsed configuration to the transverse expanded configuration, the deflectable element comprising a helically wound wire extending between the proximal end and the distal end;

manipulating the elongate member until the deflectable element in the expanded configuration contacts the proximal wall of the body lumen, thereby providing the tactile indication of the location of the distal end of the elongate member relative to the body lumen; and deploying the closure element from the distal end of the elongate member within the passage.

22. The method of claim 21, further comprising performing a diagnostic or therapeutic procedure using the one or more instruments at a location accessed via the body lumen.

23. The method of claim 22, wherein the body lumen comprises a blood vessel, and wherein the procedure comprises at least one of angioplasty, atherectomy, stent delivering, delivery of a therapeutic agent, and tissue ablation.

24. The method of claim 19, wherein the deploying step comprises advancing a housing distally along an exterior of the elongate member, the housing having the closure element detachably held thereto.

25. The method of claim 24, wherein the housing is movable between a proximal position and a distal position, the distal position being a predetermined distance from the deflectable element in its expanded configuration.

26. The method of claim 19, wherein the control element comprises a tether extending along an outer surface of at least the intermediate portion of the helically wound wire.

27. The method of claim 19, wherein at least a portion of the helically wound wire communicates with the body lumen when the helically wound wire is in the transverse expanded configuration.

28. A method for sealing a passage communicating with a body lumen using a tubular member comprising proximal and distal ends and a lumen extending therebetween, and a closure element deployable from the distal end of the tubular member, the method comprising:

advancing the distal end of the tubular member through a patient's skin into the passage towards the body lumen;

introducing a selectively expandable locator member into the lumen of the tubular member until a distal portion of the locator member extends beyond the distal end of the tubular member;

moving a control element fixedly connected to a distal portion of a deflectable element to buckle the deflectable element of the distal portion of the selectively expandable locator member from a collapsed configuration to a transversely expanded configuration within the body lumen, the deflectable element comprising a helically wound wire extending between a proximal end and a distal end and having an intermediate portion therebetween and the control element extending from the distal portion to the proximal end of the expandable locator member and extending along an outer surface of at least one coil of the helical wound wire and passing through at least one coil of the helical wound wire in a pre-deployed configuration;

manipulating the tubular member until the deflectable element in the expanded condition contacts a proximal wall of the body lumen, thereby providing a tactile indication of a location of the distal end of the tubular member relative to the body lumen; and deploying the closure element from the distal end of the tubular member within the passage, the closure element comprising a clip.

29. The method of claim 28, wherein the selectively expandable locator member is introduced into the lumen of the tubular member before the distal end of the tubular member is advanced into the passage such that the distal portion of the selectively expandable locator member is advanced through the passage into the body lumen as the distal end of the tubular member is located into the passage.

30. The method of claim 28, wherein the selectively expandable locator member is introduced into the lumen of the tubular member after the distal end of the tubular member is advanced into the passage.

31. The method of claim 28, wherein the deploying step comprises advancing a housing distally along an exterior of the elongate member, the housing having the closure element detachably held thereto.

32. The method of claim 28, wherein the buckling step comprises directing the control element coupled to the distal end of the helically wound wire proximally, the control element comprising a tether extending along an outer surface of at least the intermediate portion of the helically wound wire.

33. The method of claim 28, wherein at least a portion of the helically wound wire communicates with the body lumen when the helically wound wire is in the transversely expanded configuration.

34. A method for sealing a passage communicating with a body lumen, the method comprising:

introducing a selectively expandable locator member into the passage until a distal portion of the selectively expandable locator member extends into the body lumen;

moving a control element fixedly connected to a distal portion of a deflectable element to buckle the deflectable element on the distal portion of the selectively expandable locator member from a collapsed configuration to a transversely expanded configuration within the body lumen, the deflectable element comprising a helically wound wire extending between a proximal end and a distal end and having an intermediate portion therebetween and the control element extending from the distal portion to the proximal end of the expandable locator member and extending along an outer surface of at least one coil of the helical wound wire and passing through at least one coil of the helical wound wire in a pre-deployed configuration;

manipulating the selectively expandable locator member until the deflectable element in the expanded condition contacts a proximal wall of the body lumen;

advancing a clip having tines which extend substantially axially and distally along the selectively expandable locator member until the clip is disposed at a predetermined location relative to the distal portion of the locator member;

returning the distal portion of the selectively expandable locator member from the expanded condition to the collapsed configuration; and withdrawing the locator member from the passage, leaving the clip in the passage.

35. The method of claim 34, wherein the step of introducing the selectively expandable locator member comprises:

disposing a tubular member through a patient's skin into the passage until a distal end of the tubular member is disposed proximate the body lumen;

introducing the selectively expandable locator member into a lumen of the tubular member until the distal portion of the locator member extends beyond the distal end of the tubular member into the body lumen.

36. The method of claim 35, further comprising withdrawing the tubular member from the passage before advancing the clip into the passage.

37. The method of claim 34, wherein the step of advancing the clip comprises advancing an elongate member having the clip thereon into the passage over the selectively expandable locator member, and wherein the method further comprises deploying the clip from the elongate member at the predetermined location.

38. The method of claim 37, wherein the selectively expandable locator member and the elongate member comprise cooperating elements for identifying when the closure device reaches the predetermined location.

39. The method of claim 38, wherein the cooperating elements comprise a marker on the selectively expandable locator member having a predetermined relationship with the distal portion of the selectively expandable locator member.

40. The method of claim 37, wherein the step of advancing the clip comprises advancing a housing along the elongate member until the clip reaches the predetermined location.

41. The method of claim 37, wherein the deflectable element is collapsed during the deployment step.

42. The method of claim 41, wherein the elongate member comprises a tubular member, and wherein the distal portion of the selectively expandable locator member is retracted into the lumen after the deflectable element is collapsed.

43. The method of claim 34, wherein the clip comprises a generally annular clip having tines which extend substantially axially and distally carried on an exterior of the elongate member, and wherein advancing a clip along the selectively expandable locator member until the clip is disposed at a predetermined location relative to the distal portion of the locator member further comprises advancing the clip towards the distal end of the elongate member until tines of the clip penetrate tissue adjacent the body lumen.

44. The method of claim 34, wherein the buckling step comprises directing the control element coupled to the distal end of the helically wound wire proximally, the control element comprising a tether extending along an outer surface of at least the intermediate portion of the helically wound wire.

45. The method of claim 34, wherein at least a portion of the helically wound wire communicates with the body lumen when the helically wound wire is in the transversely expanded configuration.

46. A method for sealing a passage communicating with a body lumen using an elongate member comprising proximal and distal ends, and a closure element deployable from the distal end of the elongate member, the method comprising:

coupling a locator member to the elongate member such that a distal portion of the locator member extend distally beyond the distal end of the elongate member;

advancing the distal end of the elongate member through a patient's skin towards the body lumen via the passage until the distal portion of the locator member is located within the body lumen;

moving a control element fixedly connected to a distal portion of a deflectable element to buckle the deflectable element comprising a helically wound wire on the distal portion of the locator member from an axial collapsed configuration to a transverse expanded configuration, the helically wound wire extending between a proximal end and a distal end and having an intermediate portion therebetween and the control element extending from the distal portion to the proximal end of the locator member and extending along an outer surface of at least one coil of the helical wound wire and passing through at least one coil of the helical wound wire in a pre-deployed configuration;

manipulating the elongate member until the deflectable element in the expanded configuration contacts a proximal wall of the body lumen, thereby providing a tactile indication of a location of the distal end of the elongate member relative to the body lumen; and deploying the closure element from the distal end of the elongate member within the passage, the closure element comprising a clip.

47. The method of claim 46, further comprising withdrawing the elongate member and the locator member from the passage, leaving the closure element to substantially close the passage.

48. The method of claim 46, wherein the elongate member comprises an introducer sheath, and wherein the method further comprises introducing one or more instruments through the lumen of the sheath into the body lumen.

49. The method of claim 48, further comprising performing a diagnostic or therapeutic procedure using the one or more instruments at a location accessed via the body lumen.

50. The method of claim 48, wherein the body lumen comprises a blood vessel, and wherein the procedure comprises at least one of angioplasty, atherectomy, stent delivery, delivery of a therapeutic agent, and tissue ablation.

51. The method of claim 46, wherein the deploying step comprises advancing a housing distally along an exterior of the elongate member, the housing having the closure element detachably held thereto.

52. The method of claim 51, wherein the housing is movable between a proximal position and a distal position, the distal position being a predetermined distance from the deflectable element in its expanded configuration.

53. The method of claim 46, wherein the control element comprises a tether extending along an outer surface of at least the intermediate portion of the helically wound wire.

54. The method of claim 46, wherein at least a portion of the helically wound wire communicates with the body lumen when the helically wound wire is in the transverse expanded configuration.

* * * * *